United States Patent
Andreas

(10) Patent No.: US 8,177,831 B2
(45) Date of Patent: May 15, 2012

(54) STENT DELIVERY APPARATUS AND METHOD

(75) Inventor: Bernard Andreas, Redwood City, CA (US)

(73) Assignee: Xtent, Inc., Menlo Park, CA (US)

( * ) Notice: Subject to any disclaimer, the term of this patent is extended or adjusted under 35 U.S.C. 154(b) by 912 days.

(21) Appl. No.: 12/027,447

(22) Filed: Feb. 7, 2008

(65) Prior Publication Data
US 2008/0125850 A1    May 29, 2008

Related U.S. Application Data

(60) Division of application No. 10/794,405, filed on Mar. 3, 2004, now Pat. No. 7,351,255, which is a continuation-in-part of application No. 10/637,713, filed on Aug. 8, 2003, now Pat. No. 7,309,350, which is a continuation-in-part of application No. 10/412,714, filed on Apr. 10, 2003, now Pat. No. 7,137,993, which is a continuation-in-part of application No. 10/306,813, filed on Nov. 27, 2002, now abandoned.

(60) Provisional application No. 60/364,389, filed on Mar. 13, 2002, provisional application No. 60/336,967, filed on Dec. 3, 2001.

(51) Int. Cl.
*A61F 2/06* (2006.01)

(52) U.S. Cl. .................................... 623/1.12; 623/1.11

(58) Field of Classification Search .................. 623/1.11, 623/1.12; 604/96.01
See application file for complete search history.

(56) References Cited

U.S. PATENT DOCUMENTS

| | | | |
|---|---|---|---|
| 4,069,825 A | 1/1978 | Akiyama | |
| 4,468,224 A | 8/1984 | Enzmann et al. | |
| 4,512,338 A | 4/1985 | Balko | |
| 4,564,014 A | 1/1986 | Fogarty et al. | |
| 4,580,568 A | 4/1986 | Gianturco | |
| 4,681,110 A | 7/1987 | Wiktor | |

(Continued)

FOREIGN PATENT DOCUMENTS

DE    1 953 1659    3/1997

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Julian Woo
(74) *Attorney, Agent, or Firm* — Kilpatrick Townsend & Stockton LLP

(57) ABSTRACT

Apparatus and methods for stent delivery provide for dilatation at a treatment site as well as stent delivery, using the same stent delivery apparatus. Apparatus generally include a catheter having at least one expandable member, at least one stent positionable thereon, and a sheath disposed over the expandable member and the stent. Some embodiments include separate expandable members for dilatation of a lesion and for stent expansion, while other embodiments use the same expandable member for both. In some embodiments a stent includes multiple separable stent segments. In various embodiments, self-expanding stents may be used. Methods involve positioning a stent delivery device at a treatment site, expanding an expandable member to dilate at least a portion of a lesion at the treatment site, and expanding (or allowing to expand) a stent at the treatment site.

33 Claims, 14 Drawing Sheets

U.S. PATENT DOCUMENTS

| | | |
|---|---|---|
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,061,274 A | 10/1991 | Kensey |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A * | 11/1999 | Shmulewitz ............... 623/1.11 |
| 5,997,563 A | 12/1999 | Kretzers et al. |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |

| Patent | Kind | Date | Inventor |
|---|---|---|---|
| 6,129,756 | A | 10/2000 | Kugler |
| 6,132,460 | A | 10/2000 | Thompson |
| 6,139,572 | A | 10/2000 | Campbell et al. |
| 6,143,016 | A | 11/2000 | Bleam et al. |
| 6,156,005 | A * | 12/2000 | Theron ............... 604/96.01 |
| 6,165,167 | A | 12/2000 | Delaloye |
| 6,165,210 | A | 12/2000 | Lau et al. |
| 6,171,334 | B1 | 1/2001 | Cox |
| 6,179,878 | B1 | 1/2001 | Duering |
| 6,183,509 | B1 | 2/2001 | Dibie |
| 6,187,034 | B1 | 2/2001 | Frantzen |
| 6,190,402 | B1 | 2/2001 | Horton et al. |
| 6,196,995 | B1 | 3/2001 | Fagan |
| 6,200,337 | B1 | 3/2001 | Moriuchi et al. |
| 6,217,585 | B1 | 4/2001 | Houser et al. |
| 6,238,991 | B1 | 5/2001 | Suzuki |
| 6,241,691 | B1 | 6/2001 | Ferrera et al. |
| 6,241,758 | B1 | 6/2001 | Cox |
| 6,248,122 | B1 | 6/2001 | Klumb et al. |
| 6,251,132 | B1 | 6/2001 | Ravenscroft et al. |
| 6,251,134 | B1 | 6/2001 | Alt et al. |
| 6,254,612 | B1 | 7/2001 | Hieshima |
| 6,254,628 | B1 | 7/2001 | Wallace et al. |
| 6,258,117 | B1 | 7/2001 | Camrud et al. |
| 6,264,688 | B1 | 7/2001 | Herklotz et al. |
| 6,267,783 | B1 | 7/2001 | Letendre et al. |
| 6,270,524 | B1 | 8/2001 | Kim |
| 6,273,895 | B1 | 8/2001 | Pinchuk et al. |
| 6,273,911 | B1 | 8/2001 | Cox et al. |
| 6,273,913 | B1 | 8/2001 | Wright et al. |
| 6,287,291 | B1 | 9/2001 | Bigus et al. |
| 6,312,458 | B1 | 11/2001 | Golds |
| 6,315,794 | B1 | 11/2001 | Richter |
| 6,319,277 | B1 | 11/2001 | Rudnick et al. |
| 6,322,586 | B1 | 11/2001 | Monroe et al. |
| 6,325,823 | B1 | 12/2001 | Horzewski et al. |
| 6,334,871 | B1 | 1/2002 | Dor et al. |
| 6,340,366 | B2 | 1/2002 | Wijay |
| 6,344,272 | B1 | 2/2002 | Oldenburg et al. |
| 6,348,065 | B1 | 2/2002 | Brown et al. |
| 6,350,252 | B2 | 2/2002 | Ray et al. |
| 6,350,277 | B1 | 2/2002 | Kocur |
| 6,357,104 | B1 | 3/2002 | Myers |
| 6,361,558 | B1 | 3/2002 | Hieshima et al. |
| 6,375,676 | B1 | 4/2002 | Cox |
| 6,379,365 | B1 | 4/2002 | Diaz |
| 6,383,171 | B1 | 5/2002 | Gifford et al. |
| 6,409,753 | B1 | 6/2002 | Brown et al. |
| 6,415,696 | B1 | 7/2002 | Erickeson et al. |
| 6,416,543 | B1 | 7/2002 | Hilaire et al. |
| 6,419,693 | B1 | 7/2002 | Fariabi |
| 6,425,898 | B1 | 7/2002 | Wilson et al. |
| 6,428,811 | B1 | 8/2002 | West et al. |
| 6,451,025 | B1 | 9/2002 | Jervis |
| 6,451,050 | B1 | 9/2002 | Rudakov et al. |
| 6,464,720 | B2 | 10/2002 | Boatman et al. |
| 6,468,298 | B1 | 10/2002 | Pelton |
| 6,468,299 | B2 | 10/2002 | Stack et al. |
| 6,485,510 | B1 | 11/2002 | Camrud et al. |
| 6,488,694 | B1 | 12/2002 | Lau et al. |
| 6,488,702 | B1 | 12/2002 | Besselink |
| 6,511,468 | B1 | 1/2003 | Cragg et al. |
| 6,520,986 | B2 | 2/2003 | Martin et al. |
| 6,520,987 | B1 | 2/2003 | Plante |
| 6,527,789 | B1 | 3/2003 | Lau et al. |
| 6,527,799 | B2 | 3/2003 | Shanley |
| 6,530,944 | B2 | 3/2003 | West et al. |
| 6,540,777 | B2 | 4/2003 | Stenzel |
| 6,551,350 | B1 | 4/2003 | Thornton et al. |
| 6,555,157 | B1 | 4/2003 | Hossainy |
| 6,558,415 | B2 | 5/2003 | Thompson |
| 6,562,067 | B2 | 5/2003 | Mathis |
| 6,569,180 | B1 | 5/2003 | Sirhan et al. |
| 6,575,993 | B1 | 6/2003 | Yock |
| 6,579,305 | B1 | 6/2003 | Lashinski |
| 6,579,309 | B1 | 6/2003 | Loos et al. |
| 6,582,394 | B1 | 6/2003 | Reiss et al. |
| 6,582,460 | B1 | 6/2003 | Cryer |
| 6,585,756 | B1 | 7/2003 | Strecker |
| 6,589,273 | B1 | 7/2003 | McDermott |
| 6,592,549 | B2 | 7/2003 | Gerdts et al. |
| 6,599,296 | B1 | 7/2003 | Gillick et al. |
| 6,599,314 | B2 | 7/2003 | Mathis |
| 6,602,226 | B1 | 8/2003 | Smith et al. |
| 6,602,282 | B1 | 8/2003 | Yan |
| 6,605,062 | B1 | 8/2003 | Hurley et al. |
| 6,605,109 | B2 | 8/2003 | Fiedler |
| 6,607,553 | B1 | 8/2003 | Healy et al. |
| 6,613,074 | B1 | 9/2003 | Mitelberg et al. |
| 6,629,992 | B2 | 10/2003 | Bigus et al. |
| 6,645,517 | B2 | 11/2003 | West |
| 6,645,547 | B1 | 11/2003 | Shekalim et al. |
| 6,656,212 | B2 | 12/2003 | Ravenscroft et al. |
| 6,660,031 | B2 | 12/2003 | Tran et al. |
| 6,660,381 | B2 | 12/2003 | Halas et al. |
| 6,663,660 | B2 | 12/2003 | Dusbabek et al. |
| 6,666,883 | B1 | 12/2003 | Seguin et al. |
| 6,676,693 | B1 | 1/2004 | Belding et al. |
| 6,676,695 | B2 | 1/2004 | Solem |
| 6,679,909 | B2 | 1/2004 | McIntosh et al. |
| 6,685,730 | B2 | 2/2004 | West et al. |
| 6,692,465 | B2 | 2/2004 | Kramer |
| 6,699,280 | B2 | 3/2004 | Camrud et al. |
| 6,699,281 | B2 | 3/2004 | Vallana et al. |
| 6,699,724 | B1 | 3/2004 | West et al. |
| 6,702,843 | B1 | 3/2004 | Brown |
| 6,709,379 | B1 | 3/2004 | Brandau et al. |
| 6,709,440 | B2 | 3/2004 | Callol et al. |
| 6,712,827 | B2 | 3/2004 | Ellis et al. |
| 6,712,845 | B2 | 3/2004 | Hossainy |
| 6,723,071 | B2 | 4/2004 | Gerdts et al. |
| 6,736,842 | B2 | 5/2004 | Healy et al. |
| 6,743,219 | B1 | 6/2004 | Dwyer et al. |
| 6,743,251 | B1 | 6/2004 | Eder |
| 6,761,734 | B2 | 7/2004 | Suhr |
| 6,776,771 | B2 | 8/2004 | van Moorlegem et al. |
| 6,778,316 | B2 | 8/2004 | Halas et al. |
| 6,790,227 | B2 | 9/2004 | Burgermeister |
| 6,800,065 | B2 | 10/2004 | Duane et al. |
| 6,825,203 | B2 | 11/2004 | Pasternak et al. |
| 6,837,901 | B2 | 1/2005 | Rabkin et al. |
| 6,849,084 | B2 | 2/2005 | Rabkin et al. |
| 6,852,252 | B2 | 2/2005 | Halas et al. |
| 6,855,125 | B2 | 2/2005 | Shanley |
| 6,858,034 | B1 | 2/2005 | Hijlkema et al. |
| 6,878,161 | B2 | 4/2005 | Lenker |
| 6,884,257 | B1 | 4/2005 | Cox |
| 6,893,417 | B2 | 5/2005 | Gribbons et al. |
| 6,896,695 | B2 | 5/2005 | Mueller et al. |
| 6,913,619 | B2 | 7/2005 | Brown et al. |
| 6,918,928 | B2 | 7/2005 | Wolinsky et al. |
| 6,939,376 | B2 | 9/2005 | Shulze et al. |
| 6,945,989 | B1 | 9/2005 | Betelia et al. |
| 6,945,995 | B2 | 9/2005 | Nicholas |
| 6,951,053 | B2 | 10/2005 | Padilla et al. |
| 6,962,603 | B1 | 11/2005 | Brown et al. |
| 6,964,676 | B1 | 11/2005 | Gerberding et al. |
| 6,991,646 | B2 | 1/2006 | Clerc et al. |
| 6,994,721 | B2 | 2/2006 | Israel |
| 7,005,454 | B2 | 2/2006 | Brocchini et al. |
| 7,022,132 | B2 | 4/2006 | Kocur |
| 7,037,327 | B2 | 5/2006 | Salmon et al. |
| 7,090,694 | B1 | 8/2006 | Morris et al. |
| 7,101,840 | B2 | 9/2006 | Brocchini et al. |
| 7,131,993 | B2 | 11/2006 | Gregorich |
| 7,137,993 | B2 | 11/2006 | Acosta et al. |
| 7,141,063 | B2 | 11/2006 | White et al. |
| 7,147,655 | B2 | 12/2006 | Chermoni |
| 7,147,656 | B2 | 12/2006 | Andreas et al. |
| 7,169,172 | B2 | 1/2007 | Levine et al. |
| 7,169,174 | B2 | 1/2007 | Fischell et al. |
| 7,172,620 | B2 | 2/2007 | Gilson |
| 7,175,654 | B2 | 2/2007 | Bonsignore et al. |
| 7,182,779 | B2 | 2/2007 | Acosta et al. |
| 7,192,440 | B2 | 3/2007 | Andreas et al. |
| 7,208,001 | B2 | 4/2007 | Coyle et al. |
| 7,220,275 | B2 | 5/2007 | Davidson et al. |
| 7,220,755 | B2 | 5/2007 | Betts et al. |

| Patent/Pub. No. | Date | Name |
|---|---|---|
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,534,449 B2 | 5/2009 | Saltzman et al. |
| 7,699,886 B2 | 4/2010 | Sugimoto |
| 7,918,881 B2 | 4/2011 | Andreas et al. |
| 7,993,388 B2 | 8/2011 | Lee et al. |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0037358 A1 | 3/2002 | Barry et al. |
| 2002/0052642 A1 | 5/2002 | Cox et al. |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0137622 A1 | 6/2005 | Griffin |
| 2005/0143827 A1 | 6/2005 | Globerman et al. |
| 2005/0149168 A1 | 7/2005 | Gregorich |
| 2005/0165378 A1 | 7/2005 | Heinrich et al. |
| 2005/0182477 A1 | 8/2005 | White |
| 2005/0209674 A1 | 9/2005 | Kutscher et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0097299 A1 | 4/2008 | Andreas et al. |
| 2008/0097574 A1 | 4/2008 | Andreas et al. |

| | | | |
|---|---|---|---|
| 2008/0147162 A1 | 6/2008 | Andreas et al. | |
| 2008/0177369 A1 | 7/2008 | Will et al. | |
| 2008/0199510 A1 | 8/2008 | Ruane et al. | |
| 2008/0208311 A1 | 8/2008 | Kao et al. | |
| 2008/0208318 A1 | 8/2008 | Kao et al. | |
| 2008/0234795 A1 | 9/2008 | Snow et al. | |
| 2008/0234798 A1 | 9/2008 | Chew et al. | |
| 2008/0234799 A1 | 9/2008 | Acosta et al. | |
| 2008/0243225 A1 | 10/2008 | Satasiya et al. | |
| 2008/0249607 A1 | 10/2008 | Webster et al. | |
| 2008/0269865 A1 | 10/2008 | Snow et al. | |
| 2009/0076584 A1 | 3/2009 | Mao et al. | |
| 2009/0105686 A1 | 4/2009 | Snow et al. | |
| 2009/0149863 A1 | 6/2009 | Andreas et al. | |
| 2009/0234428 A1 | 9/2009 | Snow et al. | |
| 2009/0248137 A1 | 10/2009 | Andersen et al. | |
| 2009/0248140 A1 | 10/2009 | Gerberding | |
| 2009/0264979 A1 | 10/2009 | Kao et al. | |
| 2010/0004729 A1 | 1/2010 | Chew et al. | |

FOREIGN PATENT DOCUMENTS

| | | | |
|---|---|---|---|
| DE | 1 963 0469 | | 1/1998 |
| DE | 199 50 756 | | 8/2000 |
| DE | 101 03 000 | | 8/2002 |
| EP | 0 203 945 | B2 | 12/1986 |
| EP | 0 274 129 | B1 | 7/1988 |
| EP | 0 282 143 | | 9/1988 |
| EP | 0 505 686 | | 9/1992 |
| EP | 0 533 960 | | 3/1993 |
| EP | 0 696 447 | A2 | 2/1996 |
| EP | 0 714 640 | | 6/1996 |
| EP | 0 797 963 | A2 | 1/1997 |
| EP | 0 596 145 | | 5/1997 |
| EP | 0 947 180 | | 10/1999 |
| EP | 1 258 230 | | 11/2002 |
| EP | 1 290 987 | A2 | 3/2003 |
| EP | 1 318 765 | | 6/2003 |
| EP | 1 523 959 | A2 | 4/2005 |
| EP | 1 523 960 | A2 | 4/2005 |
| EP | 1 266 638 | B | 10/2005 |
| GB | 2277875 | A | 11/1994 |
| JP | 03-133446 | | 6/1991 |
| JP | 10-503663 | | 4/1998 |
| JP | 10-295823 | | 11/1998 |
| JP | 2001-190687 | | 7/2001 |
| JP | 2004-121343 | A | 4/2004 |
| WO | WO 94/27667 | A1 | 12/1994 |
| WO | WO 95/26695 | A2 | 10/1995 |
| WO | WO 96/33677 | | 10/1996 |
| WO | WO 96/37167 | A1 | 11/1996 |
| WO | WO 96/39077 | | 12/1996 |
| WO | WO 97/46174 | | 12/1997 |
| WO | WO 97/48351 | | 12/1997 |
| WO | WO 98/37833 | | 9/1998 |
| WO | WO 99/01087 | | 1/1999 |
| WO | WO 00/12832 | A3 | 3/2000 |
| WO | WO 00/15151 | | 3/2000 |
| WO | WO 00/32136 | | 6/2000 |
| WO | WO 00/41649 | | 7/2000 |
| WO | WO 00/50116 | | 8/2000 |
| WO | WO 00/51525 | A1 | 9/2000 |
| WO | WO 00/56237 | | 9/2000 |
| WO | WO 00/62708 | | 10/2000 |
| WO | WO 00/72780 | | 12/2000 |
| WO | WO 01/70297 | | 9/2001 |
| WO | WO 01/91918 | | 12/2001 |
| WO | WO 02/085253 | | 10/2002 |
| WO | WO 02/098326 | | 12/2002 |
| WO | WO 03/022178 | | 3/2003 |
| WO | WO 03/047651 | | 6/2003 |
| WO | WO 03/051425 | | 6/2003 |
| WO | WO 03/075797 | | 9/2003 |
| WO | WO 2004/017865 | | 3/2004 |
| WO | WO 2004/043299 | | 5/2004 |
| WO | WO 2004/043301 | | 5/2004 |
| WO | WO 2004/043510 | | 5/2004 |
| WO | WO 2004/052237 | A2 | 6/2004 |
| WO | WO 2005/009295 | | 2/2005 |
| WO | WO 2005/013853 | | 2/2005 |
| WO | WO 2007/053187 | | 5/2007 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein.

U.S. Appl. No. 09/225,364, filed Jan. 4, 1999, first named inventor: Aaron V. Kaplan.

U.S. Appl. No. 10/874,859, filed Jun. 22, 2004, first named inventor: Pablo Acosta. Abandoned.

U.S. Appl. No. 11/462,951, filed Aug. 7, 2006, first named inventor: David Snow.

U.S. Appl. No. 11/627,096, filed Jan. 25, 2007, first named inventor: Bernard Andreas.

U.S. Appl. No. 11/689,927, filed Mar. 22, 2007, first named inventor: David Snow.

U.S. Appl. No. 11/752,448, filed May 23, 2007, first named inventor: David Snow.

U.S. Appl. No. 11/771,929, filed Jun. 29, 2007, first named inventor: David Snow.

U.S. Appl. No. 11/857,562, filed Sep. 19, 2007, first named inventor: Bryan Mao.

U.S. Appl. No. 11/938,730, filed Nov. 12, 2007, first named inventor: Sunmi Chew.

U.S. Appl. No. 11/945,142, filed Nov. 26, 2007, first named inventor: Bernard Andreas.

U.S. Appl. No. 11/947,677, filed Nov. 29, 2007, first named inventor: Dan Hammersmark.

U.S. Appl. No. 11/952,644, filed Dec. 7, 2007, first named inventor: Bernard Andreas.

U.S. Appl. No. 11/953,242, filed Dec. 10, 2007, first named inventor: Bernard Andreas.

U.S. Appl. No. 12/033,586, filed Feb. 19, 2008, first named inventor: Patrick H. Ruane.

U.S. Appl. No. 12/040,598, filed Feb. 29, 2008, first named inventor: Bernard Andreas.

U.S. Appl. No. 12/061,951, filed Apr. 3, 2008, first named inventor: Stephen Kao.

Supplementary European Search Report of EP Patent Application No. 05727731.1, dated Mar. 25, 2008, 2 pages total.

"Drug Delivery Stent With Holes Located on Neutral Axis" Research Disclosure, Kenneth Mason Publications, Hampshire, CB, No. 429, Jan. 2000, p. 13.

European Search Opinion of European Patent Application No. 05727731.1, dated Apr. 9, 2009, 5 pages total.

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

Tilley, "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

\* cited by examiner

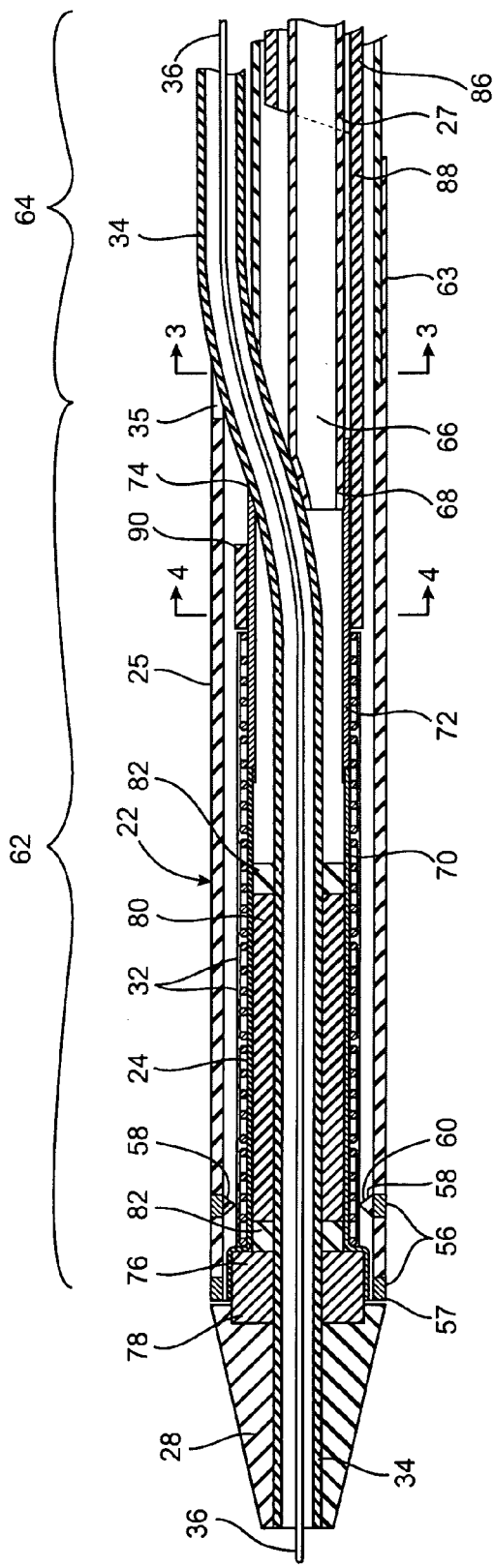
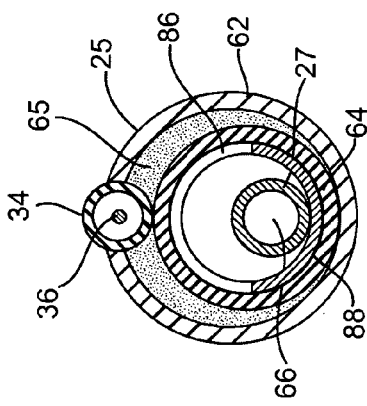
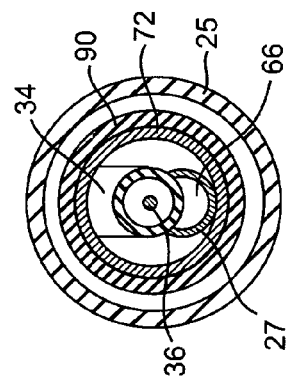

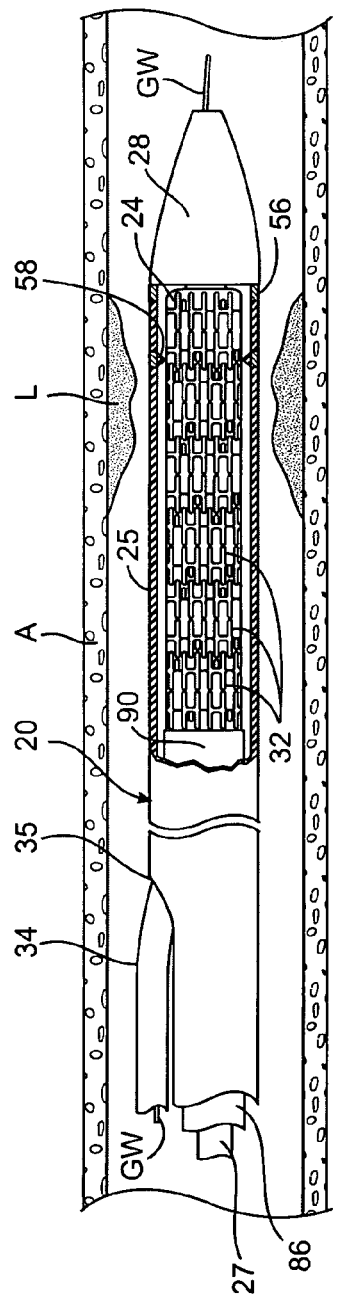
FIG. 7A
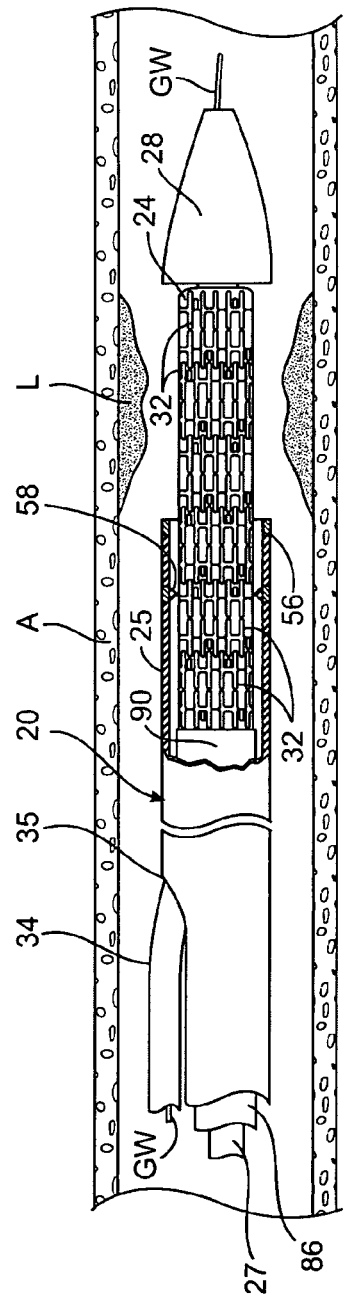
FIG. 7B
FIG. 7C

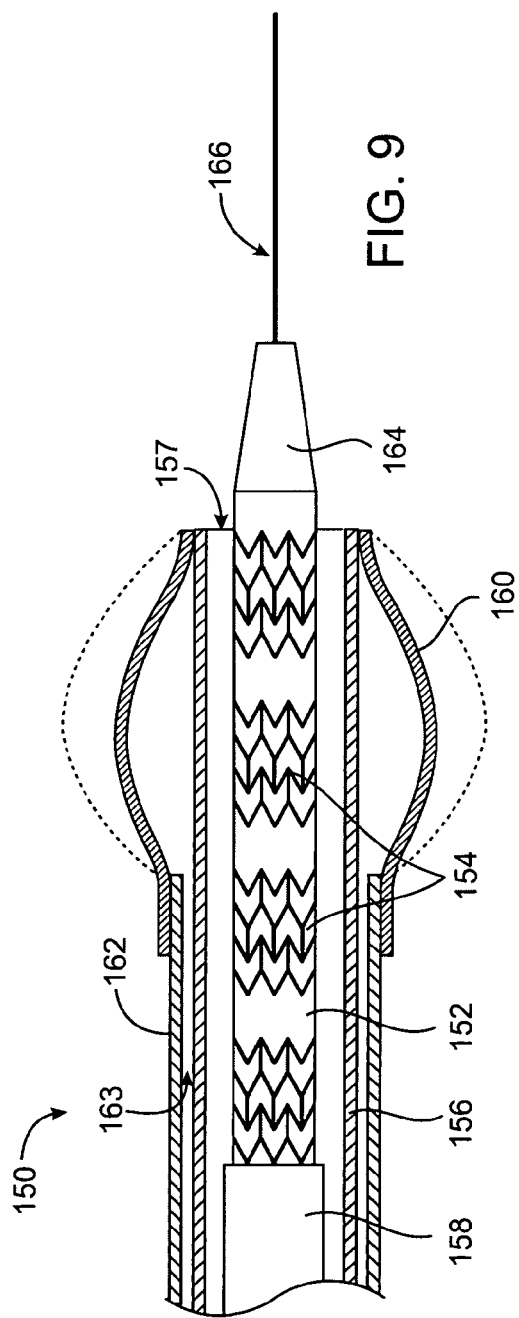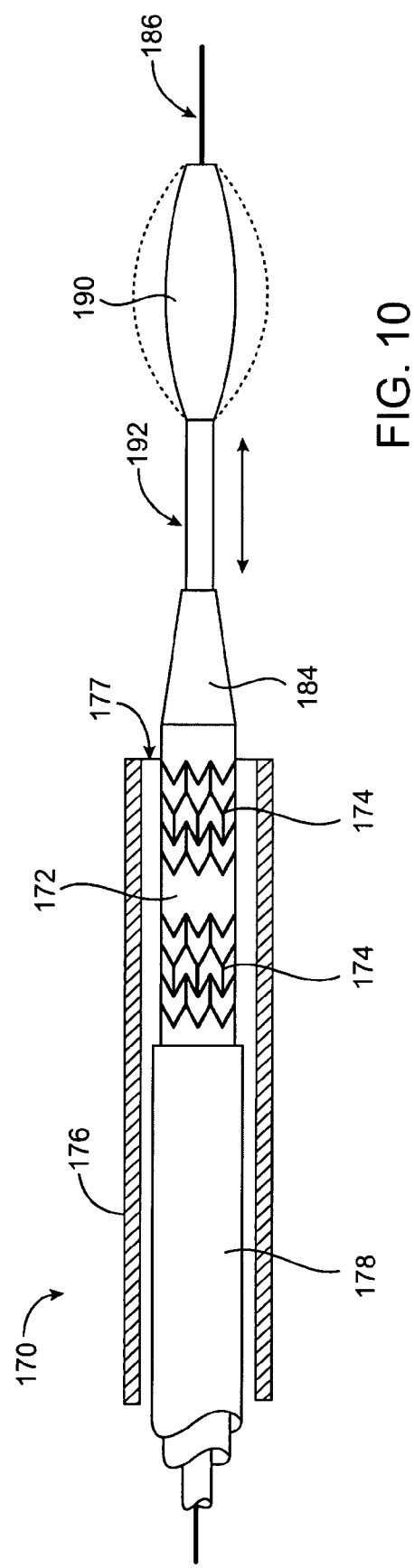

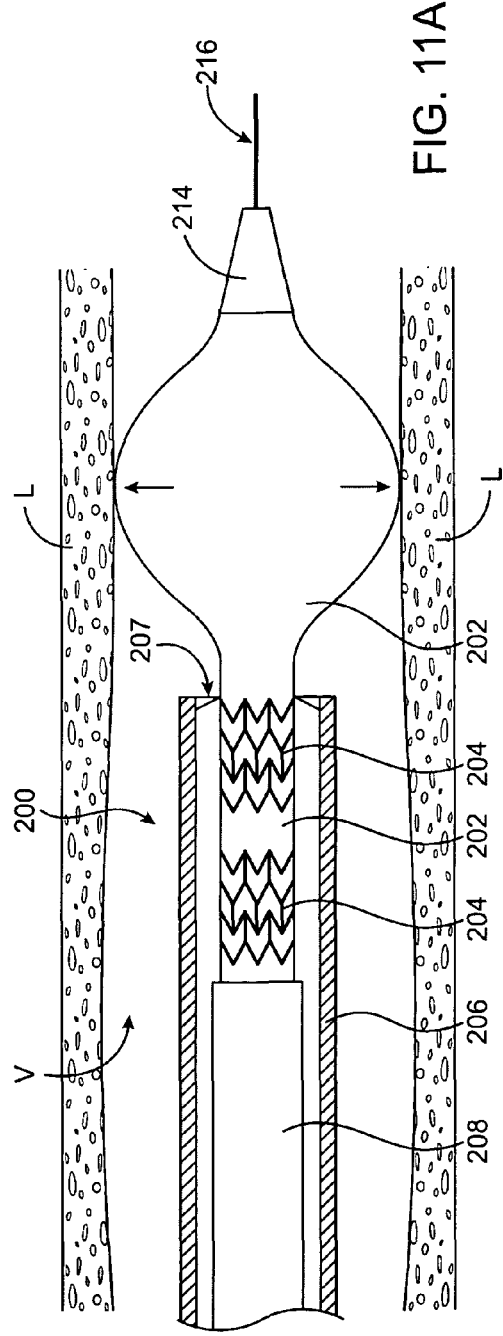
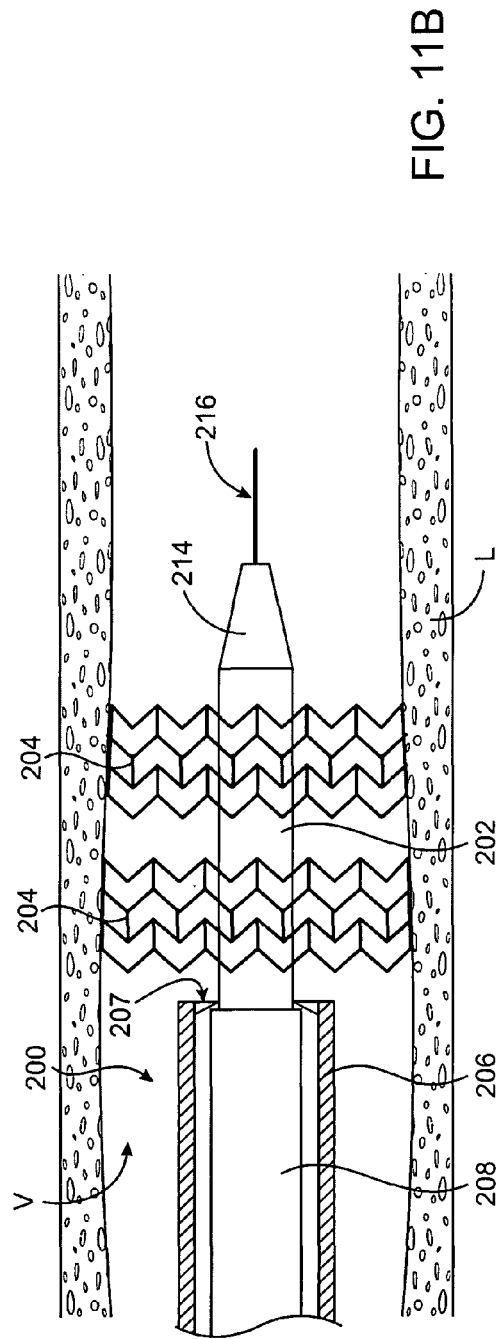

STENT DELIVERY APPARATUS AND METHOD

CROSS REFERENCE TO RELATED APPLICATIONS

The present application is a divisional of U.S. patent application Ser. No. 10/794,405 filed Mar. 3, 2004, (now U.S. Pat. No. 7,351,255) issued Apr. 1, 2008, which is a continuation-in-part of U.S. patent application Ser. No. 10/637,713, filed Aug. 8, 2003 (now U.S. Pat. No. 7,309,350) issued Dec. 18, 2007, which is a continuation-in-part of U.S. patent application Ser. No. 10/412,714, filed Apr. 10, 2003 (now U.S. Pat. No. 7,137,993) issued Nov. 21, 2006, which is a continuation-in-part of application Ser. No. 10/306,813, filed Nov. 27, 2002 now abandoned, which is a non-provisional of U.S. Provisional Patent Application Ser. Nos.: 60/336,967, filed Dec. 3, 2001, and 60/364,389, filed Mar. 13, 2002. The entire disclosures of the above-listed references are hereby fully incorporated by reference.

BACKGROUND OF THE INVENTION

The present invention relates generally to medical devices and methods. More particularly, the invention relates to apparatus and methods for independently delivering a plurality of luminal prostheses within a body lumen.

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. In recent years, however, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters, typically inserted through a femoral artery. For self-expanding stents, the stent is simply released from the delivery catheter, and it resiliently expands into engagement with the vessel wall. For balloon expandable stents, a balloon on the delivery catheter is expanded which expands and deforms the stent to the desired diameter, whereupon the balloon is deflated and removed.

Despite many recent advances in stent delivery technology, a number of shortcomings still exist. For example, current stent delivery catheters are not capable of customizing the length of the stent in situ to match the size of the lesion to be treated. While lesion size may be measured prior to stenting using angiography or fluoroscopy, such measurements may be inexact. If a stent is introduced that is found to be of inappropriate size, the delivery catheter and stent must be removed from the patient and replaced with a different device of correct size. Moreover, current stent delivery devices cannot treat multiple lesions with a single catheter. If multiple lesions are to be treated, a new catheter and stent must be introduced for each lesion to be treated.

Additionally, currently available stent delivery devices are not well-adapted for treating vascular lesions that are very long and/or in curved regions of a vessel. Current stents have a discrete length that is relatively short due to their stiffness. If such stents were made longer, to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents. Such shortcomings in the prior art are addressed by the inventions described in U.S. patent application Ser. No. 10/412,714, which is hereby fully incorporated by reference, and Ser. No. 10/637,713, which was previously incorporated by reference.

Even with improvements such as those described in the above-referenced patent applications, further improvements in stent delivery devices and methods are still being sought. For example, before a coronary stent is deployed in a stenotic lesion, the physician will typically first dilate the lesion with an angioplasty balloon. Following such "predilatation," the angioplasty catheter is removed and a stent delivery catheter is advanced to the treatment site to deploy the stent. One of the significant advantages of the stent delivery systems described in U.S. patent application Ser. Nos. 10/412,714 and 10/637,713, incorporated above, is the ability to treat multiple lesions at different locations without removing or replacing the catheter. Such a stent deliver system may be positioned at a first lesion for deployment of a first stent of a desired length, then moved to a second site where a second stent of a different length may be deployed. This may be repeated for multiple lesions without exchanging catheters, which saves time and eliminates the inefficiency of using multiple catheters. Such efficiencies are reduced, however, if it is necessary to use an angioplasty catheter to predilate lesions and a separate stent delivery catheter to deliver stents. If separate predilatation and stent delivery catheters are used, it may often be necessary to exchange, or "swap out," the two catheters multiple times during a stenting procedure.

Therefore, it would be desirable to have stent delivery systems that could be used to predilatate lesions without requiring a separate angioplasty catheter. Ideally, such stent delivery systems would allow for separate predilatation of multiple and/or long lesions as well as separate stent deployment at those lesions, without requiring any catheters to be exchanged. Preferably, such systems would also enable a user to adjust the length of the predilatation device to match the length of the lesion to be treated. At least some of these objectives will be met by the present invention.

BRIEF SUMMARY OF THE INVENTION

The invention provides apparatus and methods for delivering one or more stents into a body lumen. In one aspect of the present invention, a stent delivery device for delivering at least one stent to a treatment site includes a catheter shaft having a proximal end and a distal end, at least one stent positionable on the catheter shaft, a stent deployment mechanism for deploying at least a portion of the stent at the treatment site, and a dilatation member for dilating at least a portion of a lesion at the treatment site independently of deploying the at least one stent. The deployment mechanism generally allows the length of the deployed portion of the stent to be selected by a user. In some embodiments, the length of deployed stent may be selected in situ. Similarly, in some embodiments the length of the dilatation member to be expanded to dilate the lesion may be selected in situ.

In some embodiments, the stent deployment mechanism includes a stent expansion member coupled with the catheter shaft near the distal end and at least one axially movable sheath disposed over at least part of the stent expansion member and stent thereon. In some embodiments, the stent expansion member may also act as the dilatation member. Alternatively, the dilatation member may coupled with the sheath. In other embodiments, the dilatation member may be coupled with an inner shaft slidably disposed within the catheter shaft.

In some embodiments, the at least one stent comprises a plurality of separable stent segments. Optionally, the separable stent segments may be axially movable relative to the catheter shaft and/or the stent expansion member. Such embodiments may optionally further include a pusher member for advancing the stent segments along the catheter shaft and/or stent expansion member. In some embodiments including a sheath, as mentioned above, the sheath may be configured to constrain expansion of a first portion of the stent expansion member and a first plurality of the stent segments while allowing expansion of a second portion of the stent expansion member and a second plurality of the stent segments. Optionally, the sheath may further include at least one separation device for separating the first plurality of stent segments from the second plurality, thus allowing for expansion of a stent segment without interfering with adjacent stent segments.

In some embodiments, the dilatation member and the stent expansion member may be independently expandable. Such embodiments may optionally further include at least one inflation lumen for expanding the dilatation member. For example, in some embodiments the inflation lumen may comprise a tubular member disposed concentrically over a sheath coupled with the dilatation member. In alternative embodiments, the inflation lumen may comprise a tubular member coupled with and extending along the outer surface of a sheath coupled with the dilatation member. In other embodiments, the inflation lumen may be disposed within the wall of a sheath coupled with the dilatation member.

In another aspect of the invention, a stent delivery device for delivering at least one stent to a treatment site comprises: a catheter shaft having a proximal end and a distal end; an expandable member coupled with the catheter shaft near the distal end; at least one stent slidably positionable on the expandable member; and at least one axially movable sheath disposed over at least part of the expandable member and stent thereon. Generally, the sheath is axially movable relative to the catheter body to expose at least a portion of the expandable member without exposing the stent, and the sheath is also movable to expose at least a portion of the stent to allow it to expand.

In some embodiments, the stent is self-expanding. For example, in some embodiments, the stent comprises a plurality of separable, self-expanding stent segments. The stent (or one or more stent segments) may be advanced along the expandable member, in some embodiments, by a pusher member. Optionally, the sheath may be configured to constrain expansion of a first plurality of the stent segments while allowing expansion of a second plurality of the stent segments. In some embodiments, the sheath further comprises at least one separation device for separating the first plurality of stent segments from the second plurality, thus allowing for expansion of a stent segment without interfering with adjacent stent segments. In various embodiments, the stent segments may comprise any suitable shape memory material or the like. In one embodiment, for example, the stent segments comprise a thermal shape memory material, and the expandable member is configured to accept one or more heated or cooled fluids to change a temperature of the stent segments.

In another aspect of the invention, a stent delivery device for treating a target site in a vessel includes: a catheter shaft having a proximal end and a distal end; a first stent carried on the catheter shaft and being deployable therefrom; a second stent carried on the catheter shaft and being deployable therefrom independently of the first stent; and a dilatation member for dilating the target site independently of deploying the first and second stents.

In another aspect of the invention, a stent delivery device for delivering at least one stent to a treatment site includes: a catheter shaft having a proximal end and a distal end; a stent expansion member coupled with the catheter shaft near the distal end; at least one stent positionable on the stent expansion member; at least one axially movable sheath disposed over at least part of the stent expansion member and stent thereon; and a dilatation member coupled with the sheath for dilating one or more lesions at the treatment site. Again, the stent may comprise a plurality of separable stent segments, and the stent segments may optionally be axially movable relative to the stent expansion member. Such an embodiment may also include a pusher member for advancing the stent segments. The sheath and expandable members may have any of the features described above.

In another aspect of the present invention, a stent delivery device for delivering at least one stent to a treatment site includes: a catheter shaft having a proximal end and a distal end; at least one stent positionable on the catheter shaft; at least one axially movable sheath disposed over the catheter shaft and stent; an inner shaft slidably disposed within the catheter shaft; and a dilatation member coupled with a distal end of the inner shaft for dilating one or more lesions at the treatment site. In some embodiments, the stent may comprise a plurality of separable stent segments, and the stent segments may optionally be axially movable relative to the stent expansion member. Such an embodiment may also include a pusher member for advancing the stent segments. The sheath and expandable members may have any of the features described above.

In some embodiments, the inner shaft comprises a tubular catheter shaft. Alternatively, the inner shaft may comprise a guidewire. In some embodiments, the inner shaft is slidable to expose at least part of the dilatation member out of the distal end of the catheter shaft, and wherein the inner shaft is slidable to retract the dilatation member to a position at least partially within the catheter shaft. In some embodiments, the dilatation member is expandable while only a portion is exposed out of the distal end of the catheter shaft. In some embodiments, the dilatation member is positionable relative to the catheter shaft to adjust a length of the exposed portion of the dilatation member to dilate a desired length of the lesion at the treatment site.

Optionally, separate inflation lumens may be included for expanding either or both of the stent expansion and dilatation members. Where a separate lumen is included for expanding the dilatation member, in some embodiments the inflation lumen comprises a tubular member disposed concentrically over the inner shaft. Alternatively, the inflation lumen may comprise a tubular member disposed within the inner shaft. In other embodiments, the inflation lumen may be disposed within the wall of the inner shaft.

In yet another aspect of the present invention, a method for delivering at least one stent to a treatment site involves: positioning a distal portion of a stent delivery catheter device at the treatment site, the stent delivery catheter carrying at least one stent; expanding at least a portion of an expandable member on the catheter device to dilate at least a portion of a lesion at the treatment site; selecting a deployable portion of the stent having a selected length; and expanding the deployable portion of the stent at the treatment site, and undeployed portion of the stent remaining in the delivery catheter. Some embodiments may optionally further involve positioning the deployable portion of the stent over the expandable member.

In some embodiments, expanding the deployable portion of the stent comprises expanding the expandable member. In some embodiments, the at least one stent comprises a plurality of stent segments, and retracting the sheath exposes at least one of the stent segments to self-expand at the treatment site. Such embodiments may optionally further include, after retracting the sheath: positioning the expandable member within the at least one self-expanded stent segment; and expanding at least a portion of the expandable member to further expand the stent segment.

In some embodiments, the method may also involve exposing the portion of the expandable member outside the sheath before the expanding step. The method may optionally further include retracting the portion of the expandable member to a position within the sheath after the expanding step. Some embodiments may also involve passing a fluid through the expandable member while the stent segments are disposed thereon, wherein the stent segments comprise a thermal shape memory material, and wherein passing the fluid changes the temperature of the stent segments. For example, in some embodiments the passed fluid is heated to a temperature higher than body temperature, while in others it is cooled to a temperature lower than body temperature. In some embodiments, the portion of the expandable member is expanded using fluid.

In another aspect of the invention, a method for delivering at least one stent to a treatment site includes: positioning a distal portion of a stent delivery catheter device at the treatment site, the stent delivery catheter carrying at least one stent; expanding at least a portion of a dilatation member of the catheter device to dilate at least a portion of a lesion at the treatment site; and expanding at least a portion of a stent expansion member of the catheter device to deploy at least a portion of the at least one stent at the treatment site. The method may optionally further include selecting a deployable portion of the stent, wherein the deployable portion is expanded by the stent expansion member while an undeployed portion of the stent remains unexpanded in the stent delivery catheter. Again, in some embodiments the at least one stent comprises a plurality of stent segments, and deploying at least the portion comprises deploying at least one of the stent segments.

In some embodiments, the dilatation member is disposed on an outer surface of a sheath slidably disposed over the stent and the stent expansion member. In such embodiments, the method may also include retracting the sheath to expose at least the portion of the stent expansion member and at least one stent. Alternative embodiments may further involve sliding an inner shaft of the catheter device distally relative to the stent expansion member to expose at least the portion of the dilatation member, the dilatation member being disposed on the inner shaft. In some embodiments, such a method may also include sliding the catheter body distally over the inner shaft to position the stent expansion member at the treatment site. Optionally, the dilatation member may then be re-expanded at the treatment site after the stent is deployed.

Further aspects of the nature and advantages of the invention will become apparent from the detailed description below taken in conjunction with the drawings.

BRIEF DESCRIPTION OF THE DRAWINGS

FIG. 2A is a side cross-section of a distal portion of the stent delivery catheter of FIG. 1 with expandable member deflated and sheath advanced distally.

FIG. 3 is a transverse cross-section through line 3-3 of FIG. 2A.

FIG. 4 is a transverse cross-section through line 4-4 of FIG. 2A.

FIGS. 7A-7E are side cut-away views of the stent delivery catheter of the invention positioned in a vessel with the stent segments of FIGS. 5A-5B, illustrating various steps of delivering a prosthesis according to the method of the invention.

FIG. 9 is a side cut-away view of a stent delivery catheter having an expandable member disposed on a sheath according to one embodiment of the invention.

FIG. 10 is a side cut-away view of a stent delivery catheter having an expandable member disposed on a slidable inner shaft according to one embodiment of the invention.

FIGS. 11A and 11B are side cut-away views of a stent delivery catheter being used to dilate a lesion and place stent segments in the lesion according to one embodiment of the invention.

DETAILED DESCRIPTION OF THE INVENTION

Figure 1:
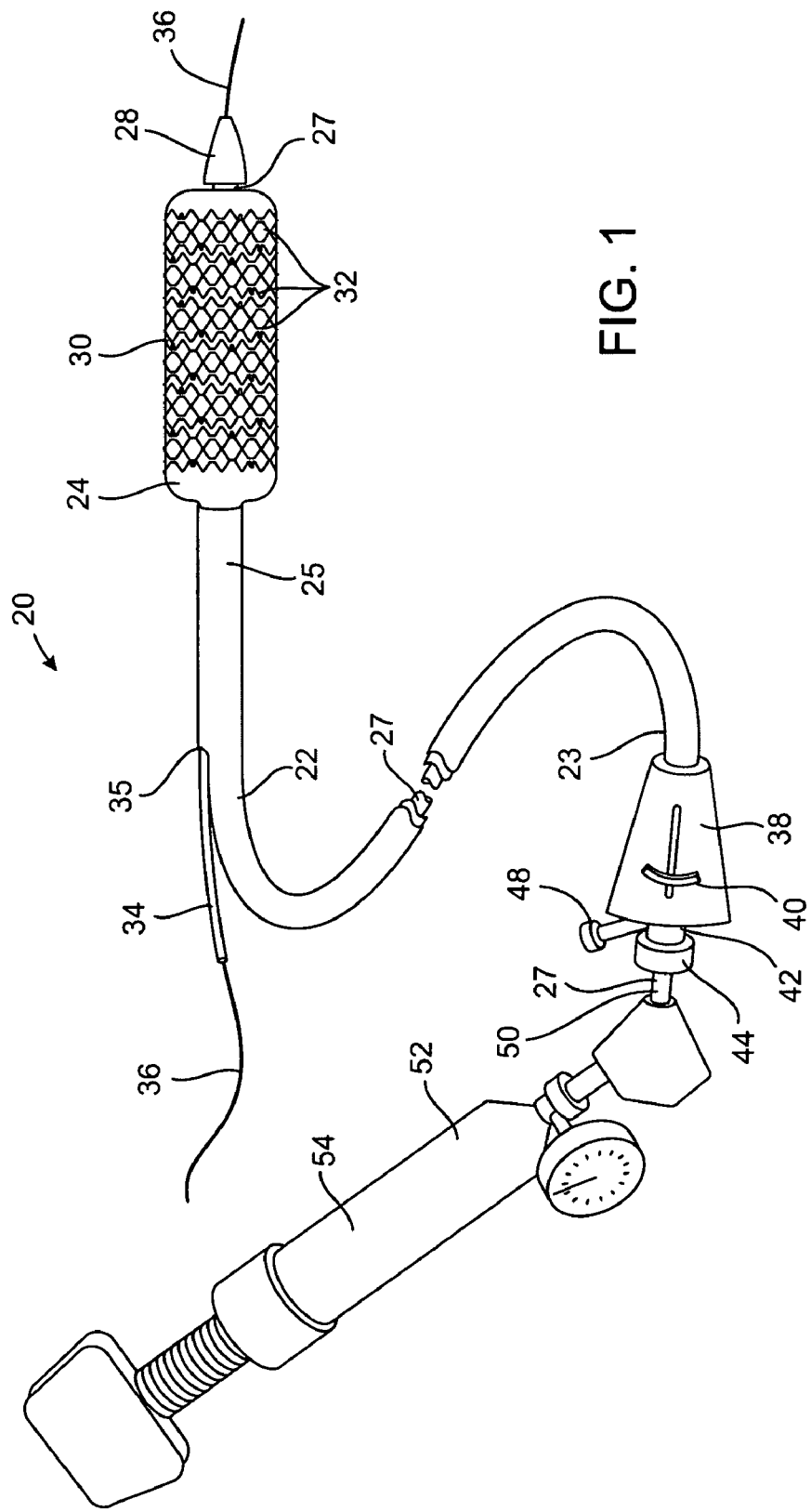
FIG. 1 is a perspective view of a stent delivery catheter according to the invention with sheath retracted and expandable member inflated.

One embodiment of a stent delivery catheter according to present invention is illustrated in FIG. 1. Stent delivery catheter 20 includes a catheter body 22 comprising an outer sheath 25 slidably disposed over an inner shaft 27. An expandable member 24, preferably an inflatable balloon (shown in an inflated configuration), is mounted to inner shaft 27 and is exposed by retracting sheath 25 relative to inner shaft 27. A tapered nosecone 28, composed of a soft elastomeric material to reduce trauma to the vessel during advancement of the device, is mounted distally of expandable member 38. A stent 30, which preferably comprises a plurality of separate or separable stent segments 32, is disposed on expandable member 24 for expansion therewith. A guidewire tube 34 is slidably positioned through a guidewire tube exit port 35 in sheath 25 proximal to expandable member 24. A guidewire 36 is positioned slidably through guidewire tube 34, expandable member 24, and nosecone 28 and extends distally thereof.

A handle 38 is mounted to a proximal end 23 of sheath 25 and includes an actuator 40 slidably mounted thereto for purposes described below. An adaptor 42 is mounted to the proximal end of handle 38 and provides a catheter port 44 through which inner shaft 27 is slidably positioned. A flush port 48 is mounted to the side of adaptor 42 through which a fluid such as saline can be introduced into the interior of catheter body 22. An annular seal (not shown) in catheter port 44 seals around inner shaft 27 to prevent fluid from leaking through catheter port 44. Optionally, a clamp (not shown) such as a threaded collar, can be mounted to catheter port 44 to lock inner shaft 27 relative to handle 38.

Inner shaft 27 has a proximal end 50 to which is mounted an inflation adaptor 52. Inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. Inflation adaptor 52 is in fluid communication with expandable member 24 via an inflation lumen (described below) in inner shaft 27 to enable inflation of expandable member 24.

Referring now to FIGS. 2A-2B, 3 and 4, which show a distal portion of the stent delivery catheter in cross-section, it may be seen that sheath 25 may be extended up to nosecone 28 to fully surround expandable member 24 and stent segments 32. One or more radiopaque markers 56 are mounted near a distal end 57 of sheath 25 to facilitate visualization of the position of sheath 25 using fluoroscopy. In a preferred embodiment, two annular markers 56 are spaced apart a length equal to the length of one of stent segments 32 for purposes described more fully below. Sheath 25 further includes a valve member 58 preferably spaced proximally from distal end 57 a distance equal to the length of one of stent segments 32. Valve member 58 has an inwardly extending flange 60 configured to frictionally engage stent segments 32 and thereby restrict the sliding movement of stent segments 32 distally relative to sheath 25. Flange 60 may be a polymeric material integrally formed with sheath 25 or a separate annular member bonded or otherwise mounted to sheath 25. Various embodiments of valve member 58 are described in copending application Ser. No. 10/412,714, Filed Apr. 10, 2003, which is incorporated herein by reference.

Sheath 25 has a distal extremity 62 configured to surround expandable member 24 and stent segments 32 disposed thereon when in an unexpanded configuration. Distal extremity 62 extends proximally to a junction 63, preferably aligned with the location of guidewire tube exit port 35, where distal extremity 62 is joined to a proximal extremity 64 that extends proximally to handle 38 (see FIG. 1). In a preferred embodiment, distal extremity 62 has a length of about 15-35 cm and proximal extremity 64 as a length of about 100-125 cm. Proximal extremity 64 may be constructed of a variety of biocompatible polymers or metals, preferably being stainless steel or Nitinol. Distal extremity 62 may be a polymer such as PTFE, FEP, polyimide, or Pebax, and is preferably reinforced with a metallic or polymeric braid to resist radial expansion when expandable member 24 is expanded.

Preferably, proximal extremity 64 has a smaller transverse dimension than distal extremity 62 to accommodate the added width of guidewire tube 34 within the vessel lumen, as well as to maximize flexibility and minimize profile. In one embodiment, shown in FIG. 3, distal extremity 62 is a tubular member having a first outer diameter, preferably about 1.0-1.5 mm, and proximal extremity 64 is a tubular member having a second, smaller outer diameter, preferably about 0.7-1.0 mm. At the junction of proximal extremity 64 with distal extremity 62, a proximally-facing crescent-shaped opening 65 is formed between the two tubular members that creates guidewire tube exit port 35. Excess space within crescent-shaped opening 65 may be filled with a filler material such as adhesive.

In an alternative embodiment (not shown), a hole is formed in the sidewall of distal extremity 62 or proximal extremity 64 to create guidewire tube exit port 35. Proximally of guidewire tube exit port 35, the wall of sheath 25 adjacent to guidewire tube 34 is flattened or collapsible inwardly thereby reducing the transverse dimension of sheath 25 to accommodate the width of guidewire tube 34.

Guidewire tube 34 is slidably positioned through guidewire tube exit port 35. Preferably, guidewire tube exit port 35 is configured to provide a total or partial fluid seal around the periphery of guidewire tube 34 to limit blood flow into the interior of sheath 25 and to limit leakage of saline (or other flushing fluid) out of sheath 25. This may be accomplished by sizing guidewire tube exit port 35 appropriately so as to form a fairly tight frictional seal around guidewire tube 34 while still allowing the sliding motion thereof relative to sheath 25. Alternatively an annular sealing ring may be mounted in guidewire tube exit port 35 to provide the desired seal.

Guidewire tube exit port 35 will be positioned to provide optimal tracking of stent delivery catheter 20 through the vasculature and maximizing the ease with which the catheter can be inserted onto and removed from a guidewire to facilitate catheter exchanges. Usually, guidewire tube exit port 35 will be positioned at a location proximal to expandable member 24 when sheath 25 is extended fully distally up to nosecone 28, but a distance of no more than one-half the length of sheath 25 from distal end 57. In preferred embodiments for coronary applications, guidewire tube exit port 35 is spaced proximally a distance of about 20-35 cm from the distal end 57 of sheath 25.

Guidewire tube 34 should extend proximally from guidewire tube exit port 35 a distance at least as long as the longest possible stent that may be deployed, e.g. 30-60 mm, to allow for retraction of sheath 25 that distance while retaining a portion of guidewire tube 34 external to sheath 25. Preferably guidewire tube 34 extends proximally a distance of about 3-15 cm from guidewire tube exit port 35 when sheath 25 is in a fully distal position, with the proximal end thereof disposed a distance of about 23-50 cm from the distal tip of nosecone 28. Where stent delivery catheter 20 is to be positioned through a guiding catheter, the proximal end of guidewire tube 34 will preferably be positioned so as to be within the guiding catheter when expandable member 24 is positioned at the target site for stent deployment. Guidewire tube 34 is preferably a highly flexible polymer such as PTFE, FEP, polyimide, or Pebax, and may optionally have a metal or polymer braid embedded in it to increase kink-resistance.

Inner shaft 27 forms an inflation lumen 66 that is in communication with interior of expandable member 24. In the distal extremity of stent delivery catheter 20 inner shaft 27 is preferably formed of a polymer such as PTFE, FEP, polyimide, or Pebax, and may be reinforced with a metallic braid for added radial strength and kink resistance. In the proximal extremity of delivery catheter 20, inner shaft 27 may be a similar polymer or a metal such as stainless steel or Nitinol.

Expandable member 24 has an expandable balloon member 70 that is joined to a non-expandable tubular leg 72. Expandable balloon member 70 is a semi-compliant polymer such as Pebax or Nylon. Tubular leg 72 is preferably a polymer such as polyimide, PTFE, FEP or Pebax and may optionally be reinforced with a metal or polymer braid. Tubular leg 72 has an open proximal end 74 through which guidewire tube 34 extends. Proximal end 74 of tubular leg 72 is fixed to distal end 68 of inner shaft 27 and to guidewire tube 34, forming a fluid-tight seal. Balloon member 70 has a distal end 76 bonded to an annular stop 78, which is mounted to nosecone 28. Stop 78 has a size and shape selected to engage stent segment 32 and provide a stop against which stent segments 32 can be located in the ideal deployment position without being pushed beyond the distal end of balloon member 70. Guidewire tube 34 passes through the interior of balloon member 70 and is mounted to nosecone 28, thereby providing a passage through the distal portion of catheter body 22 through which guidewire 36 may pass.

Optionally, within the interior of balloon member 70 an annular base member 80 is mounted to guidewire tube 34 and has a diameter selected to urge balloon member 70 against stent segments 32 in their unexpanded configuration, thereby providing frictional engagement with stent segments 32. This helps to limit unintended sliding movement of stent segments 32 on balloon member 70. Base member 80 may be made of a soft elastomer, foam, or other compressible material. Adjacent to the distal and proximal ends of base member 80 two annular radiopaque markers 82 are mounted to guidewire tube 34, facilitating visualization of the location of balloon member 70 with fluoroscopy and enabling appropriate positioning of stent segments 32 on balloon member 70. Alternatively, only a single marker 82 at the distal end of base member 80 may be used, or markers may be placed at other locations on nosecone 28, guidewire tube 34, or inner shaft 27. Such markers may be made of various radiopaque materials such as platinum/iridium, tantalum, and other materials.

Stent segments 32 are slidably positioned over balloon member 70. Depending upon the number of stent segments 32 loaded in stent delivery catheter 20, stent segments 32 may be positioned over both balloon member 70 and tubular leg 72. In an exemplary embodiment, each stent segment is about 2-8 mm in length, and up to 10-50 stent segments may be positioned end-to-end in a line over balloon member 70 and tubular leg 72. Stent segments 32 preferably are in direct contact with each other, but alternatively separate spacing elements may be disposed between adjacent stent segments, the spacing elements being movable with the stent segments along balloon member 70. Such spacing elements may be plastically deformable or self-expanding so as to be deployable with stent segments 32 into the vessel, but alternatively could be configured to remain on balloon member 70 following stent deployment; for example, such spacing elements could comprise elastic rings which elastically expand with balloon member 70 and resiliently return to their unexpanded shape when balloon member 70 is deflated. The spacing elements could be pushed to the distal end of balloon member 70 against stop 78 as additional stent segments 32 are advanced distally.

Stent segments 32 are preferably a malleable metal so as to be plastically deformable by expandable member 24 as they are expanded to the desired diameter in the vessel. Alternatively, stent segments 32 may be formed of an elastic or super elastic shape memory material such as Nitinol so as to self-expand upon release into the vessel by retraction of sheath 25. Stent segments 32 may also be composed of polymers or other suitable biocompatible materials. In self-expanding embodiments, expandable member 24 may also be used for predilatation of a lesion prior to stent deployment and/or for augmenting the expansion of the self-expanding stent segments, as is described in greater detail below. In some embodiments, stent segments 32 may be formed of a thermal shape memory material, and expandable member 24 may be used for accepting a heated or cooled fluid while in contact with stent segments 32 so as to change the temperature of the stent segments 32, causing them to expand upon release. In some embodiments, expandable member 24, when containing cooled fluid, may be further used to help expand a lesion after stent segments 32 are in place.

In preferred embodiments, stent segments 32 are coated with a drug that inhibits restenosis, such as Rapamycin, Paclitaxel, analogs, prodrugs, or derivatives of the foregoing, or other suitable agent, preferably carried in a bioerodible polymeric carrier. Alternatively, stent segments 32 may be coated with other types of drugs and therapeutic materials such as antibiotics, thrombolytics, anti-thrombotics, anti-inflammatories, cytotoxic agents, anti-proliferative agents, vasodilators, gene therapy agents, radioactive agents, immunosuppressants, and chemotherapeutics. Such materials may be coated over all or a portion of the surface of stent segments 32, or stent segments 32 may include apertures, holes, channels, or other features in which such materials may be deposited.

Stent segments 32 may have a variety of configurations, including those described in copending application Ser. No. 60/440,839, filed Jan. 17, 2003, which is incorporated herein by reference. Other preferred stent configurations are described below. Stent segments 32 are preferably completely separate from one another without any interconnections, but alternatively may have couplings between two or more adjacent segments which permit flexion between the segments. As a further alternative, one or more adjacent stent segments may be connected by separable or frangible couplings that are separated prior to or upon deployment, as described in copending application Ser. No. 10/306,813, filed Nov. 27, 2002, which is incorporated herein by reference.

Figure 2B:
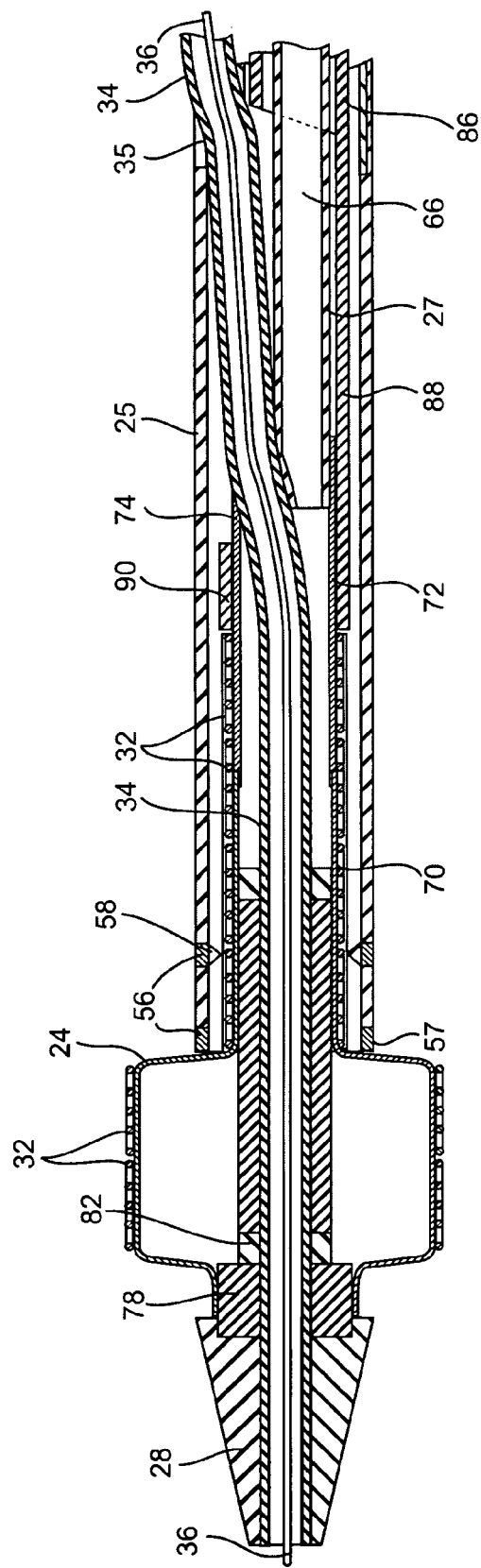
FIG. 2B is a side cross-section of a distal portion of the stent delivery catheter of FIG. 1 with expandable member inflated and sheath retracted.

A pusher tube 86 is slidably disposed over inner shaft 27 and has a distal extension 88 coupled to a pusher ring 90. Pusher ring 90 is slidable over tubular leg 72 and engages the stent segment 32 at the proximal end of the line of stent segments 32. At its proximal end (not shown), pusher tube 86 is coupled to sliding actuator 40 on handle 38 (see FIG. 1). In this way, pusher tube 86 can be advanced distally relative to inner shaft 27 to urge stent segments 32 distally over expandable member 24 (or pusher tube 86 may be held in position while retracting expandable member 24 relative to stent segments 32) until the stent segments engage stop 78. In addition, pusher tube 86 can be used to hold stent segments 32 in place on expandable member 24 while sheath 25 is retracted to expose a desired number of stent segments 32, as shown in FIG. 2B. Pusher tube 86 may be constructed of a variety of biocompatible polymers or metals, preferably being stainless steel or Nitinol. Distal extension 88 and pusher ring 90 may be a polymer such as PTFE, FEP, polyimide, or Pebax, and are preferably reinforced with a metallic or polymeric braid to resist radial expansion when expandable member 24 is expanded.

It can be seen that with sheath 25 retracted a desired distance, expandable member 24 is allowed to expand when inflation fluid is delivered through inflation lumen 66, thereby expanding a desired number of stent segments 32 exposed distally of sheath 25. The remaining portion of expandable member 24 and the remaining stent segments 32 within sheath 25 are constrained from expansion by sheath 25.

FIG. 2B further illustrates that when sheath 25 is retracted relative to expandable member 24, guidewire tube exit port 35 becomes further away from the point at which guidewire 36 exits the proximal end 74 of tubular leg 72, increasing the distance that guidewire 36 must pass within the interior of sheath 25. Advantageously, guidewire tube 34 provides a smooth and continuous passage from the tubular leg 72 through guidewire tube exit port 35, eliminating any problems that might result from changing the alignment of the two. This is particularly important in the present invention where the stent delivery catheter may carry a large number of stent segments 32 and sheath 25 may be retracted a substantial distance relative to expandable member 24, resulting in substantial misalignment of guidewire tube exit port 35 relative to tubular leg 72.

Figure 5A:
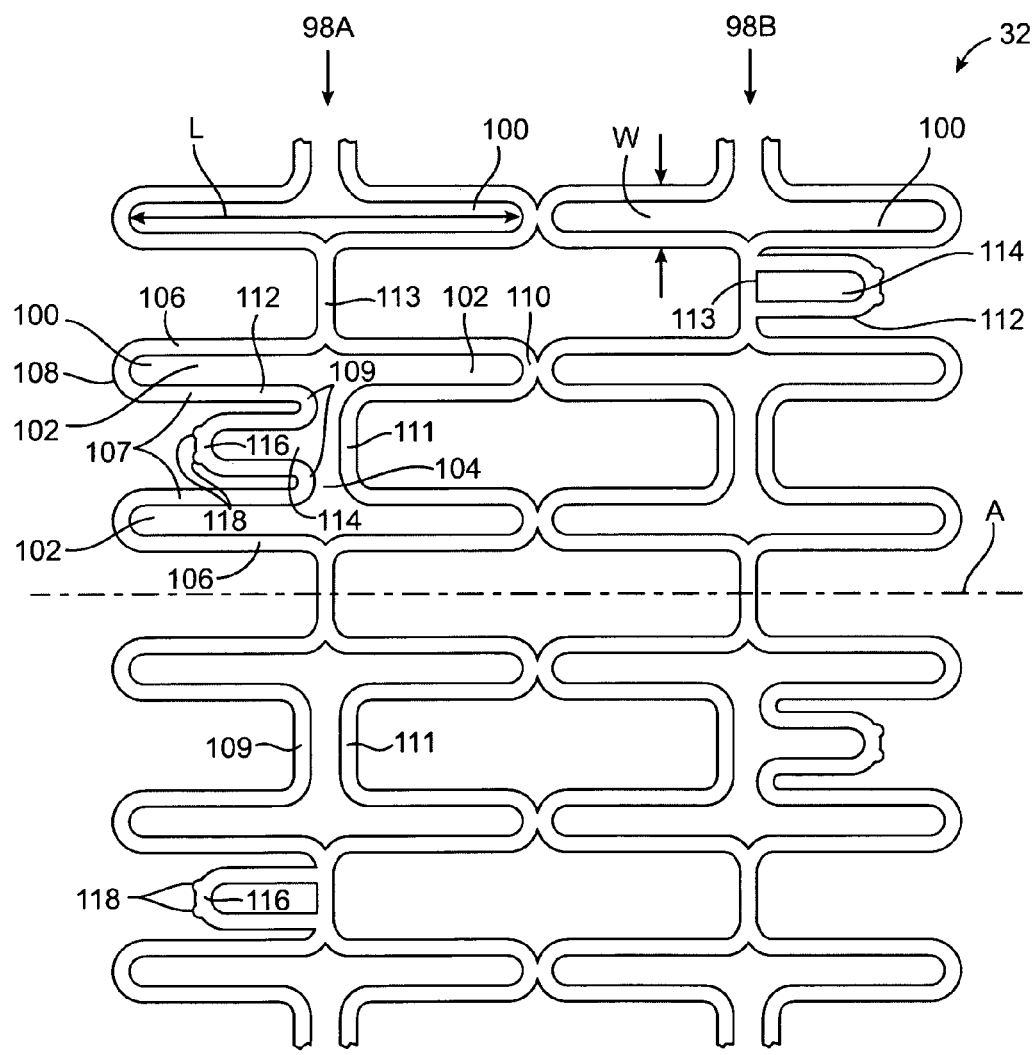
FIG. 5A is a side view of a first embodiment of a stent segment according to the invention in an unexpanded configuration.
Figure 5B:
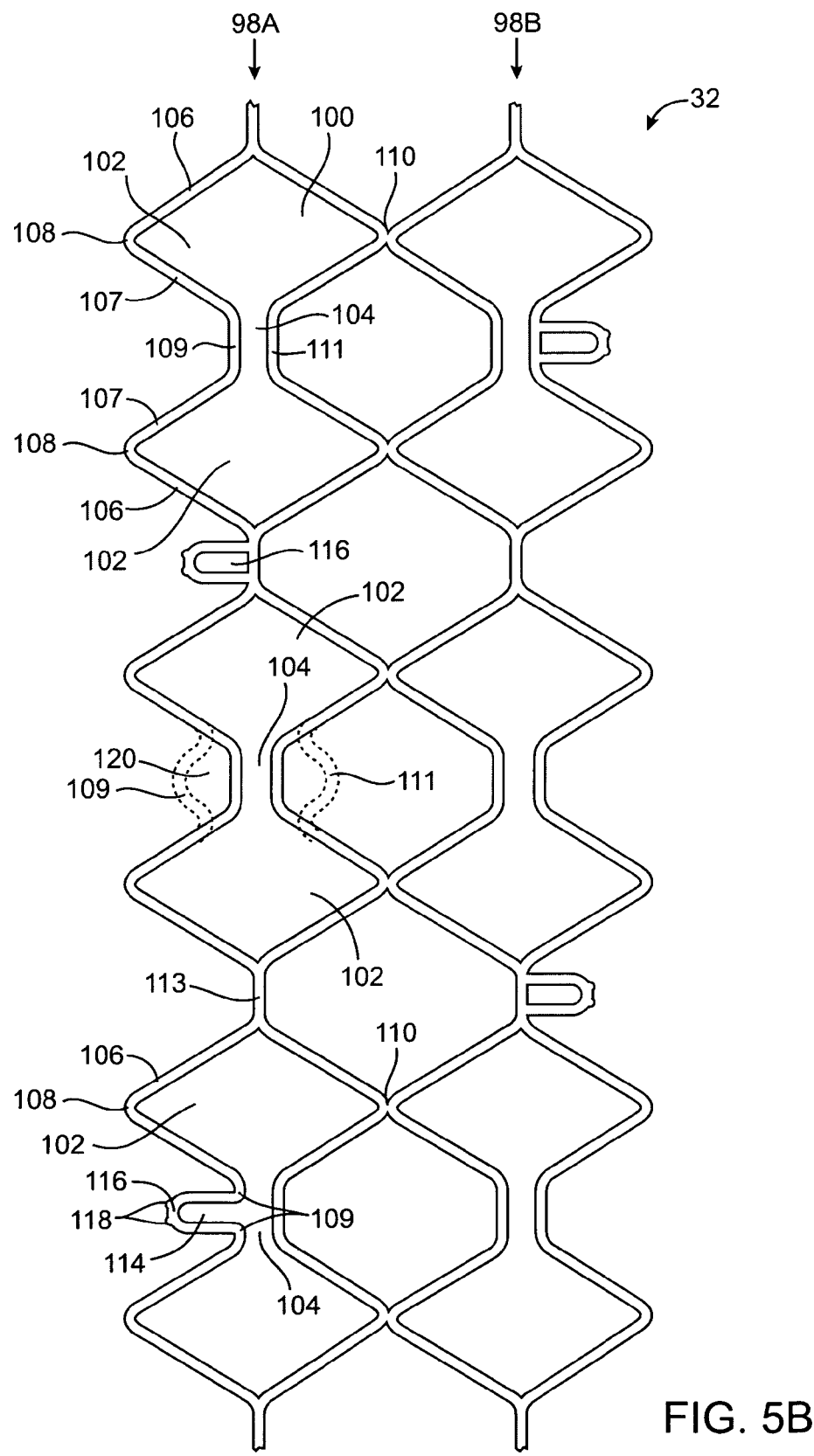
FIG. 5B is a side view of the stent segment of FIG. 5A in an expanded configuration.

In order to confirm the positioning of stent segments 32 on expandable member 24, fluoroscopy is used to visualize stent segments 32 relative to markers 82 on inner shaft 27. In addition, by fluoroscopic visualization of markers 56 on sheath 25 the user can see the extent of retraction of sheath 25 relative to expandable member 24 and view the location of the exposed stent segments 32 relative to sheath 25. Visualization of stent segments 32 is further enhanced with the use of radiopaque markers and/or materials in or on the stent segments themselves. Markers of radiopaque materials may be applied to the exterior of stent segments 32, e.g., by applying a metal such as gold, platinum, a radiopaque polymer, or other suitable coating or mark on all or a portion of the stent segments. Alternatively, stent segments 32 may include a radiopaque cladding or coating or may be composed of radiopaque materials such as L-605 cobalt chromium (ASTM F90), other suitable alloys containing radiopaque elements, or multilayered materials having radiopaque layers. In yet another alternative, stent segments 32 may have a geometry conducive to fluoroscopic visualization, such as having struts of greater thickness, sections of higher density, or overlapping struts. Some of the possible materials that may be used in stent segments 32 include (by ASTM number):

F67-00 Unalloyed Titanium
F75-01 Cobalt-28 Chromium-6 Molybdenum Alloy
F90-01 Wrought Cobalt-20 Chromium-15 Tungsten-10 Nickel Alloy
F136-02a Wrought Titanium-6 Aluminum-4 Vanadium ELI Alloy
F138-00, F139-00 Wrought 18 Chromium-14 Nickel-2.5 Molybdenum Stainless Steel Bar or Sheet
F560-98 Unalloyed Tantalum
F562-02 Wrought 35 Cobalt-35 Nickel-20 Chromium-10 Molybdenum Alloy
F563-00 Wrought Cobalt-20 Nickel-20 Chromium 3.5 Molybdenum-3.5 Tungsten-5 Iron Alloy
F688 Wrought Cobalt-35 Nickel-20 Chromium-10 Molybdenum Alloy
F745-00 18 Chromium-12.5 Nickel-2.5 Molybdenum Stainless Steel
F799-02 Cobalt-28 Chromium-6 Molybdenum Alloy
F961-96 Cobalt-35 Nickel-20 Chromium-10 Molybdenum Alloy
F1058-02 Wrought 40 Cobalt-20 Chromium-16 Iron-15 Nickel-7 Molybdenum Alloy
F1091-02 Wrought Cobalt-20 Chromium-15 Tungsten-10 Nickel Alloy
F1108 Titanium-6 Aluminum-4 Vanadium Alloy
F1295-01 Wrought Titanium-6 Aluminum-7 Niobium Alloy
F1314-01 Wrought Nitrogen-strengthened 22 Chromium-13 Nickel-5 Manganese-2.5 Molybdenum Stainless Steel Alloy
F1241-99 Unalloyed Titanium Wire
F1350-02 Wrought 18 Chromium-14 Nickel-2.5 Molybdenum Stainless Steel Wire
F1377-98a Cobalt-28 Chromium-6 Molybdenum Powder coating
F1472-02a Wrought Titanium-6 Aluminum-4 Vanadium Alloy
F1537-00 Wrought Cobalt-28 Chromium-6 Molybdenum Alloy
F1580-01 Titanium and Titanium-6 Aluminum-4 Vanadium Alloy Powder coating
F1586-02 Wrought Nitrogen Strengthened 21 Chromium-10 Nickel-3 Manganese-2.5 Molybdenum Stainless Steel Bar
F1713-96 Wrought Titanium-13 Niobium-13 Zirconium Alloy
F1813-01 Wrought Titanium-12 Molybdenum-6 Zirconium-2 Iron Alloy
F2063-00 Wrought Nickel-Titanium Shape Memory Alloys
F2066-01 Wrought Titanium-15 Molybdenum Alloy
F2146-01 Wrought Titanium-3 Aluminum-2.5 Vanadium Alloy Seamless Tubing
F2181-02a Wrought Stainless Steel Tubing A first preferred geometry of stent segments 32 is illustrated in FIGS. 5A-5B. FIG. 5A illustrates a portion of a stent segment 32 in an unexpanded configuration, shown in a planar shape for clarity. Stent segment 32 comprises two parallel rows 98A, 98B of I-shaped cells 100 formed around an axis A so that stent segment 32 has a cylindrical shape. Each cell 100 has upper and lower axial slots 102 aligned with the axial direction and a circumferential slot 104. Upper and lower slots 102 preferably have an oval, racetrack, rectangular or other oblong shape with a long dimension L generally parallel to axis A and a short dimension W perpendicular thereto. Axial slots 102 are bounded by upper axial struts 106 and lower axial struts 107, curved outer ends 108 and curved inner ends 110. Each circumferential slot 104 is bounded by an outer circumferential strut 109 and an inner circumferential strut 111. Each I-shaped cell 100 is connected to the adjacent I-shaped cell 100 in the same row 98A or 98B by a circumferential connecting strut 113. All or a portion of cells 100 in row 98A merge or join with cells 100 in row 98B at the inner ends 110, which are integrally formed with the inner ends 110 of the adjacent cells 100.

In a preferred embodiment, a spacing member 112 extends outwardly in the axial direction from a selected number of outer circumferential struts 109 and/or connecting struts 113. Spacing member 112 preferably itself forms a subcell 114 in its interior, but alternatively may be solid without any cell or opening therein. For those spacing members 112 attached to outer circumferential struts 109, subcell 114 preferably communicates with I-shaped cell 100. Spacing members 112 are configured to engage the curved outer ends 108 of an adjacent stent segment 32 so as to maintain appropriate spacing between adjacent stent segments. In one embodiment, spacing members 112 have outer ends 116 with two spaced-apart protrusions 118 that provide a cradle-like structure to index and stabilize the curved outer end 108 of the adjacent stent segment. Preferably, spacing members 112 have an axial length of at least about 10%, more preferably at least about 25%, of the long dimension L of I-shaped cells 100, so that the I-shaped cells 100 of adjacent stent segments are spaced apart at least that distance. Because spacing members 112 experience little or no axial shortening during expansion of stent segments 32, this minimum spacing between stent segments is maintained both in the unexpanded and expanded configurations.

FIG. 5B shows stent segment 32 of FIG. 5A in an expanded configuration. It may be seen that cells 100 are expanded so that upper and lower slots 102 are diamond shaped with circumferential slots 104 remaining basically unchanged. This results in some axial shortening of the stent segment, thereby increasing the spacing between adjacent stent segments. The stent geometry is optimized by balancing the amount of axial shortening and associated inter-segment spacing, the desired degree of vessel wall coverage, the desired metal density, and other factors. Because the stent is comprised of multiple unconnected stent segments 32, any desired number from 2 up to 10 or more stent segments may be deployed simultaneously to treat lesions of any length. Further, because such segments are unconnected to each other, the deployed stent structure is highly flexible and capable of deployment in long lesions having curves and other complex shapes.

As an additional feature, circumferential slots 104 provide a pathway through which vessel side branches can be accessed for catheter interventions. Should stent segment 32 be deployed at a location in which it covers the ostium of a side branch to which access is desired, a balloon dilatation catheter may be positioned through circumferential slot 104 and expanded. This deforms circumferential struts 109, 111 axially outward, thereby expanding circumferential slot 104 and further expanding upper and lower slots 102, as shown in phantom in FIG. 3B. This provides a relatively large opening 120 through which a catheter may be inserted through stent segment 32 and into the side branch for placing stents, performing angioplasty, or carrying out other interventions.

Figure 6A:
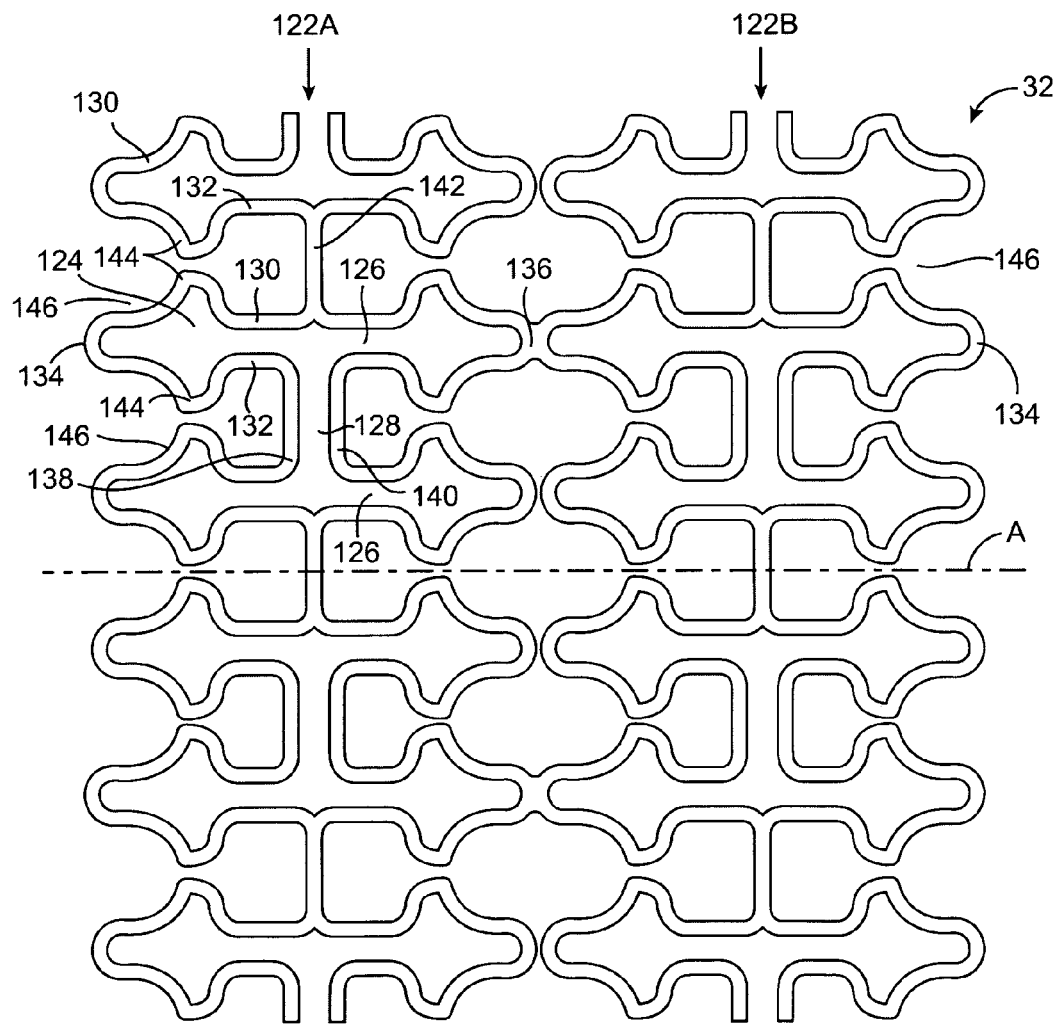
FIG. 6A is a side view of a second embodiment of a stent segment according to the invention in an unexpanded configuration.
Figure 6B:
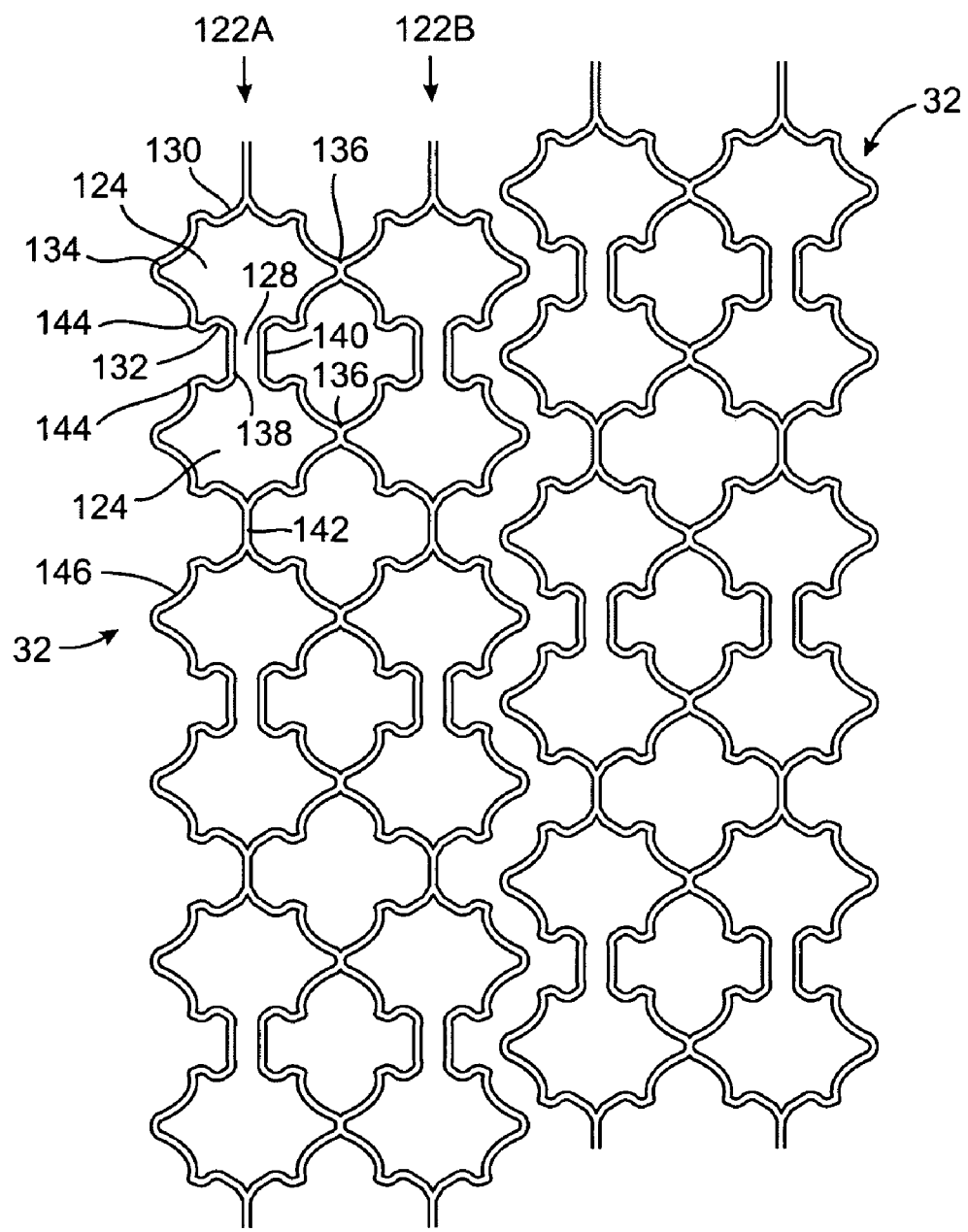
FIG. 6B is a side view of two of the stent segments of FIG. 6A in an expanded configuration.

FIGS. 6A-6B illustrate a second embodiment of a stent segment 32 according to the invention. In FIG. 6A, a portion of stent segment 32 is shown in a planar shape for clarity. Similar to the embodiment of FIG. 5A, stent segment 32 comprises two parallel rows 122A, 122B of I-shaped cells 124 formed into a cylindrical shape around axial axis A. Cells 124 have upper and lower axial slots 126 and a connecting circumferential slot 128. Upper and lower slots 126 are bounded by upper axial struts 130, lower axial struts 132, curved outer ends 134, and curved inner ends 136. Circumferential slots 128 are bounded by outer circumferential strut 138 and inner circumferential strut 140. Each I-shaped cell 124 is connected to the adjacent I-shaped cell 124 in the same row 122 by a circumferential connecting strut 142. Row 122A is connected to row 122B by the merger or joining of curved inner ends 136 of at least one of upper and lower slots 126 in each cell 124.

One of the differences between the embodiment of FIGS. 6A-6B and that of FIGS. 5A-5B is the way in which spacing is maintained between adjacent stent segments. In place of the spacing members 112 of the earlier embodiment, the embodiment of FIG. 6A includes a bulge 144 in upper and lower axial struts 130, 132 extending circumferentially outwardly from axial slots 126. These give axial slots 126 an arrowhead or cross shape at their inner and outer ends. The bulge 144 in each upper axial strut 130 extends toward the bulge 144 in a lower axial strut 132 in the same cell 100 or in an adjacent cell 100, thus creating a concave abutment 146 in the space between each axial slot 126. Concave abutments 146 are configured to receive and engage curved outer ends 134 of cells 124 in the adjacent stent segment, thereby maintaining spacing between the stent segments. The axial location of bulges 144 along upper and lower axial struts 130, 132 may be selected to provide the desired degree of inter-segment spacing.

FIG. 6B shows two stent segments 32 of FIG. 6A in an expanded condition. It may be seen that axial slots 124 are deformed into a circumferentially widened modified diamond shape with bulges 144 on the now diagonal upper and lower axial struts 130, 132. Circumferential slots 128 are generally the same size and shape as in the unexpanded configuration. Bulges 144 have been pulled away from each other to some extent, but still provide a concave abutment 146 to maintain a minimum degree of spacing between adjacent stent segments. As in the earlier embodiment, some axial shortening of each segment occurs upon expansion and stent geometry can be optimized to provide the ideal intersegment spacing.

It should also be noted that the embodiment of FIGS. 6A-6B retains the feature described above with respect to FIGS. 5A-5B to enable access to vessel side branches blocked by stent segment 32. Should such side branch access be desired, a dilatation catheter may be inserted into circumferential slot 128 and expanded to provide an enlarged opening through which a side branch may be entered. Other preferred geometries for stent segments 32 are described in U.S. patent application Ser. No. 10/738,666, with is hereby fully incorporated by reference.

Referring now to FIGS. 7A-7E, the use of the stent delivery catheter of the invention will be described. While the invention will be described in the context of coronary artery treatment, the invention is useful in any of a variety of blood vessels and other body lumens in which stents are deployed, including the carotid, femoral, iliac and other arteries, as well as veins and other fluid-carrying vessels. A guiding catheter (not shown) is first inserted into a peripheral artery such as the femoral and advanced to the ostium of the target coronary artery. A guidewire GW is then inserted through the guiding catheter into the coronary artery A where lesion L is to be treated. The proximal end of guidewire GW is then inserted through nosecone 28 and guidewire tube 34 outside the patient's body and stent delivery catheter 20 is slidably advanced over guidewire GW and through the guiding catheter into the coronary artery A. Stent delivery catheter 20 is positioned through a lesion L to be treated such that nosecone 28 is distal to lesion L. During this positioning, sheath 25 is positioned distally up to nosecone 28 so as to surround expandable member 24 and all of the stent segments 32 thereon.

Optionally, lesion L may be predilated prior to stent deployment. Predilatation may be performed prior to introduction of stent delivery catheter 20 by inserting an angioplasty catheter over guidewire GW and dilating lesion L. Alternatively, stent delivery catheter 20 may be used for predilitation by retracting sheath 25 along with stent segments 32 to expose an extremity of expandable member 24 long enough to extend through the entire lesion. This may be done while delivery catheter 20 is positioned proximally of lesion L or with expandable member 24 extending through lesion L. Fluoroscopy enables the user to visualize the extent of sheath retraction relative to lesion L by observing the position of marker 56 on sheath 25 relative to marker 82 at the distal end of expandable member 24. To allow stent segments 32 to move proximally relative to expandable member 24, force is released from pusher tube 86 and valve member 58 engages and draws the stent segments proximally with sheath 25. With the appropriate length of expandable member 24 exposed, expandable member 24 is positioned within lesion L and inflation fluid is introduced through inflation lumen 66 to inflate expandable member 24 distally of sheath 25 and thereby dilate lesion L. Expandable member 24 is then deflated and retracted within sheath 25 while maintaining force on pusher tube 86 so that stent segments 32 are positioned up to the distal end of expandable member 24, surrounded by sheath 25. Alternative embodiments of devices and methods for lesion predilatation are described in detail below.

Following any predilatation, stent delivery catheter 20 is repositioned in artery A so that nosecone 28 is distal to lesion L as shown in FIG. 7A. Sheath 25 is then retracted as in FIG. 7B to expose the appropriate number of stent segments 32 to cover lesion L. Again, fluoroscopy can be used to visualize the position of sheath 25 by observing marker 56 thereon relative to marker 82 within expandable member 24. As sheath 25 is drawn proximally, force is maintained against pusher tube 86 so that stent segments 32 remain positioned up to the distal end of expandable member 24. It should also be noted that sheath 25 moves proximally relative to guidewire tube 34, which slides through guidewire tube exit port 35. Advantageously, regardless of the position of sheath 25, guidewire tube 34 provides a smooth and continuous passage for guidewire GW so that stent delivery catheter slides easily over guidewire GW. Optionally, a distal portion of expandable member 24 may have a different size of may be made of a different material or different polymeric formulation than the remainder of expandable member 24 so as to be more suited for pre- or post-dilatation. For example, the distal portion of expandable member 24 may be less compliant than the remainder of the expandable member and/or may be made of a more hard or durable polymer suited to higher-pressure inflation for displacement of stenotic material.

With the desired number of stent segments 32 exposed distally of sheath 25, it is frequently desirable to create some spacing between the stent segments to be deployed and those remaining enclosed within sheath 25. This reduces the risk of dislodging or partially expanding the distal-most stent segment 32 within sheath 25 when expandable member 24 is inflated. Such spacing is created, as shown in FIG. 7C, by releasing force against pusher tube 86 and retracting sheath 25 further proximally a short distance. The engagement of valve member 58 with stent segments 32 moves those stent segments 32 within sheath 25 away from those stent segments 32 distal to sheath 25. The length of this spacing is preferably equal to the length of about ½-1 stent segment.

Figure 7D:
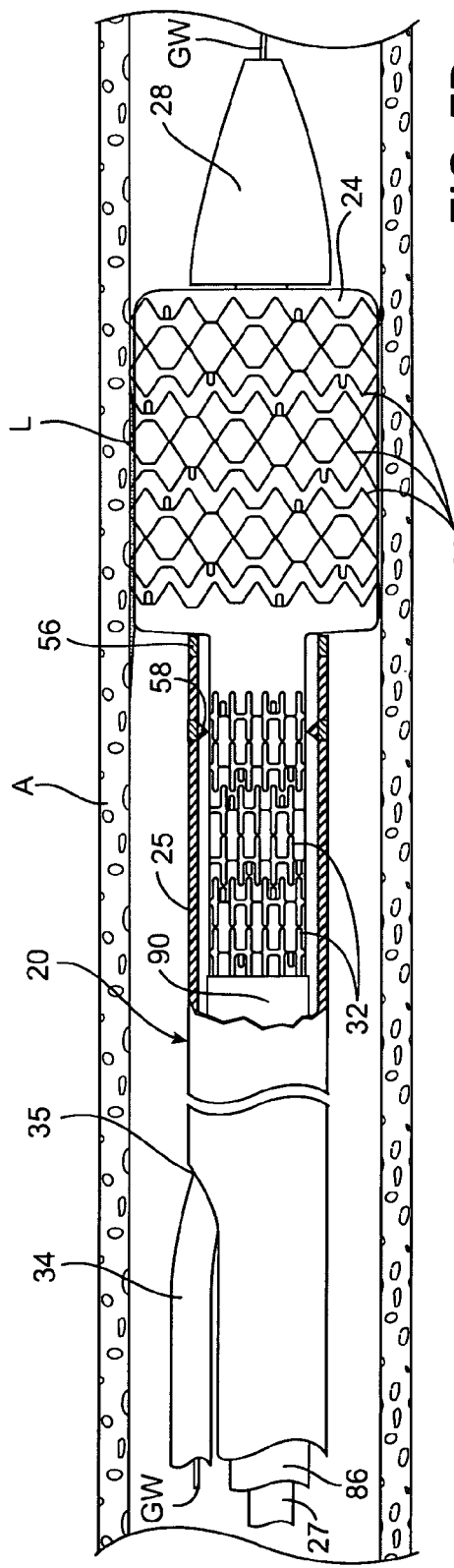

Expandable member 24 is then inflated by delivering inflation fluid through inflation lumen 66, as shown in FIG. 7D. The exposed distal portion of expandable member 24 expands so as to expand stent segments 32 thereon into engagement with lesion L. If predilatation was not performed, lesion L may be dilated during the deployment of stent segments 32 by appropriate expansion of expandable member 24. Sheath 25 constrains the expansion of the proximal portion of expandable member 24 and those stent segments 32 within sheath 25.

Figure 7E:
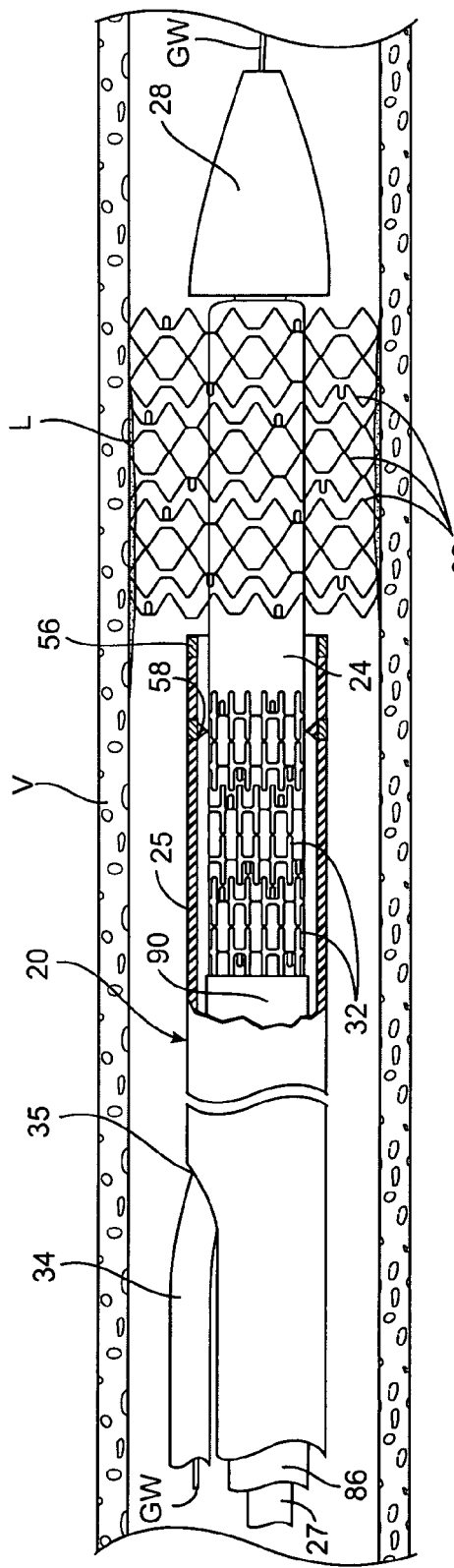
Figure 8:
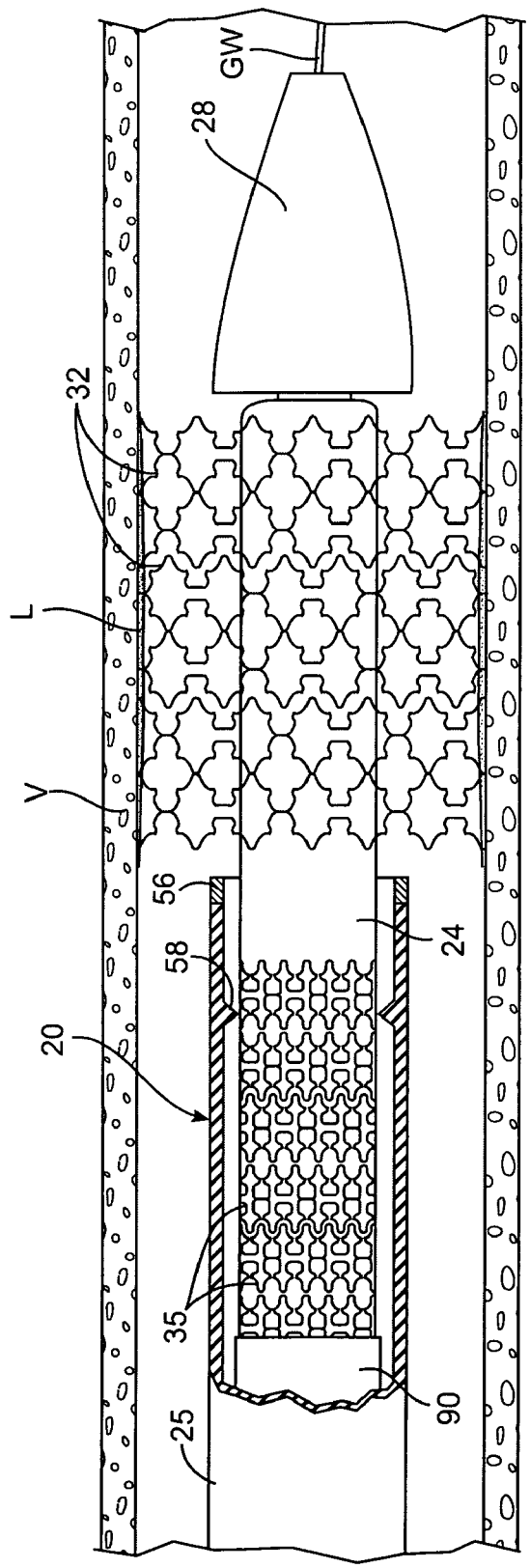
FIG. 8 is a side cut-away view of the stent delivery catheter of the invention positioned in a vessel with the stent segments of FIGS. 6A-6B in a deployed configuration.

Expandable member 24 is then deflated, leaving stent segments 32 in a plastically-deformed, expanded configuration within lesion L, as shown in FIG. 7E. The alternative embodiment of stent segment 32 illustrated in FIGS. 6A-6B is shown in a similarly expanded condition in FIG. 8. With stent segments 32 deployed, expandable member 24 may be retracted within sheath 25, again maintaining force against pusher tube 86 to position stent segments 32 at the distal end of expandable member 24. Expandable member 24 is moved proximally relative to stent segments 32 until the distal-most stent segment engages stop 78 (FIGS. 2A-2B), thereby placing stent segments 32 in position for deployment. Stent delivery catheter 20 is then ready to be repositioned at a different lesion in the same or different artery, and additional stent segments may be deployed. During such repositioning, guidewire tube 34 facilitates smooth tracking over guidewire GW. Advantageously, multiple lesions of various lengths may be treated in this way without removing stent delivery catheter 20 from the patient's body. Should there be a need to exchange stent delivery catheter 20 with other catheters to be introduced over guidewire GW, guidewire tube 34 facilitates quick and easy exchanges.

When the movement of the pusher tube, sheath, or stent segments is described in relation to other components of the delivery catheter of the invention, such movement is relative and will encompass both moving the sheath, pusher tube, or stent segments while keeping the other component(s) stationary, keeping the sheath, pusher tube or stent segments stationary while moving the other component(s), or moving multiple components simultaneously relative to each other.

Referring now to FIG. 9, one embodiment of a stent delivery catheter device 150 suitably includes a stent expansion member 152 over which a stent having multiple stent segments 154 may be positioned, an inner sheath 156 disposed over stent segments 154 and stent expansion member 152, a pusher member 158 for slidably advancing stent segments 154 along expansion member 152, a nosecone 164, and a dilatation member 160 coupled with an outer sheath 162. Inner sheath may include a stent separation member 157 for separating adjacent stent segments 154. Outer sheath 162 may be disposed over inner sheath 156 to form an inflation lumen 163 for expanding dilation member 160. Alternatively, the inflation lumen may be disposed within the wall of inner sheath 156, or it may comprise a tube or lumen fixed or molded on the exterior wall of inner sheath 156. As with other embodiments previously described, catheter device 150 may be delivered over a guidewire 166.

Stent delivery catheter device 150 could be used similarly to many of the embodiments described above, with the additional feature of using dilatation member 160 to pre-dilate a lesion before placing one or more stent segments 154 at the lesion. Additionally, after pre-dilatation and stent segment placement, dilatation member 160 may also be positioned, in its deflated form, within one or more expanded stent segments 154 and expanded to further expand stent segments 154, to confirm complete expansion of stent segments 154, to further dilate the lesion and/or the like. Outer sheath 162 and inner sheath 156 are typically retractable together to expose one or more stent segments 154 and/or a portion of stent expansion member 152. Stent separation member 157 may be used to separate adjacent stent segments 154, to retract slidable stent segments 154 over stent expansion member 152, and/or to hold stent segments 154 in place while stent expansion member 152 is advanced. In the embodiment shown in FIG. 9, stent segments 154 may alternatively be self-expanding, wherein inner sheath 156 restrains stent segments 154 from expansion until it is retracted to allow one or more of the stent segments to self-expand into the lesion at the treatment site.

Referring now to FIG. 10, another embodiment of a stent delivery catheter device 170 may include a stent expansion member 172, a stent having stent segments 174 positionable on stent expansion member 172, a sheath 176 disposed over expandable member 172 and stent segments 174 and having a stent separation member 177, a pusher member 178, a nosecone 184, a slidable inner shaft 192, and a dilatation member 190 disposed along slidable inner shaft 192. Again, catheter device 170 may be advanced along a guidewire 186. In alternative embodiments, low-profile, flexible shaft may be fixed to and extend distally from nosecone 184, rather than being slidable, with dilatation member 190 coupled to its distal end. Alternatively, a dilatation member may be coupled with the nosecone itself, and/or the like.

Slidable inner shaft 192 may be moved axially in distal and proximal directions (two-headed arrow) to expose all or a portion of dilatation member 190 and to retract all or a portion back into nosecone 184 and/or first expandable member 172. In an alternative embodiment, dilatation member 190 may be significantly longer than the one shown in FIG. 10 (for example, about 30-100 mm), such that only a portion of dilatation member 190 is typically advanced out of the distal end of nosecone 184. This allows the user to adjust the length of the expanded portion of second expandable member 190 so as to match the length of the lesion being dilated. Nosecone 184 restrains the unexposed portion of second expandable member 190 from expansion while the exposed distal portion is expanded. In any case, dilatation member 190 may be used to pre-dilate a lesion before placing stent segments 174 and may also be used to further expand the placed segments 174, further expand a lesion after placement of segments 174 and/or the like.

FIGS. 11A and 11B demonstrate a method for dilating a lesion L in a vessel V and placing stent segments according to one embodiment. In this embodiment, a stent delivery catheter device 200 is positioned in a vessel V in a location for treating a lesion L, for example by passing device 200 over a guidewire 216 or by any other suitable positioning method. A sheath 206 may then be retracted and/or an expandable member 202 may be advanced to expose a portion of expandable member 202 distally of sheath 206. As sheath 206 is retracted, a stent separation/retaining member 207 may slide stent segments 204 proximally relative to expandable member 202 to expose a desired length of expandable member 202 coextensive with lesion L. The exposed portion of expandable member 202, without stent segments 202 thereon, may then be expanded (solid-tipped arrows) to pre-dilate the lesion. Expandable member 202 may then be deflated/unexpanded and retracted back into a position within stent segments 204. Alternatively or additionally, sheath 206 and pusher 208 may be used to slidably advance stent segments 204 over the now-unexpanded expandable member 202.

As shown in FIG. 11B, sheath 206 may next be retracted to expose both stent segments 204 and expandable member 202. The number of stent segments 204 and the length of expandable member 202 are selected to match the length of the lesion L. In some embodiments, stent segments 204 self-expand to contact the lesion L, while in other embodiments, stent segments 204 are expanded by expandable member 202. Once stent segments 204 are expanded, expandable member 202 may optionally be re-expanded to further expand segments 204, assure that segments 204 are fully expanded, further expand lesion L or the like. In some embodiments, further lesions along the vessel V may be additionally treated by repositioning device 200, pre-dilating the additional lesion(s), placing stent segments, and the like.

Figure 12A:
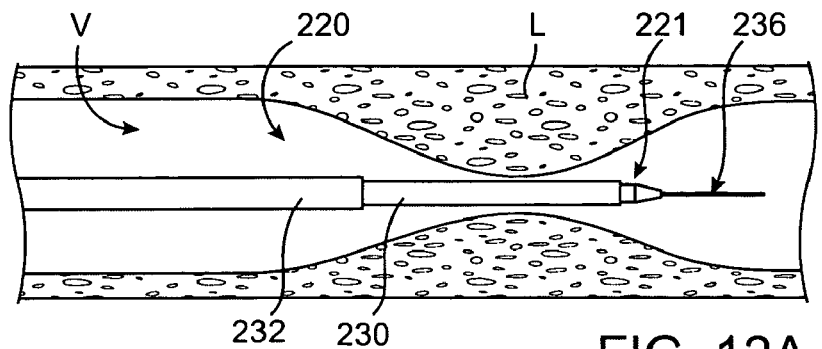
FIGS. 12A-12E are side views of a stent delivery catheter being used in a vessel to dilate a lesion and place stent segments in the lesion according to one embodiment of the invention.
Figure 12B:
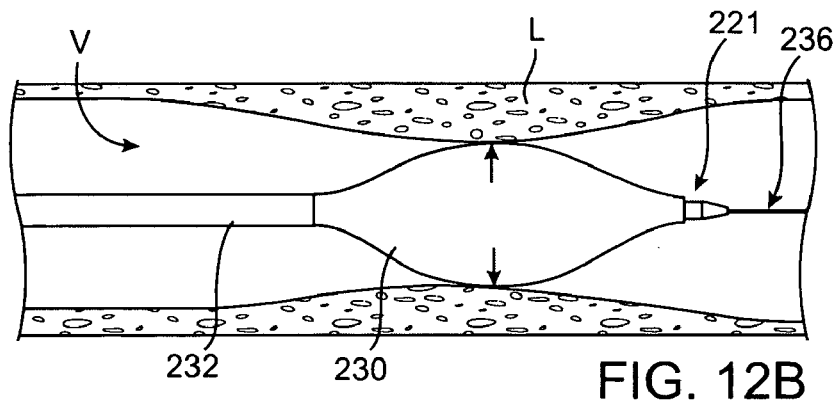
Figure 12C:
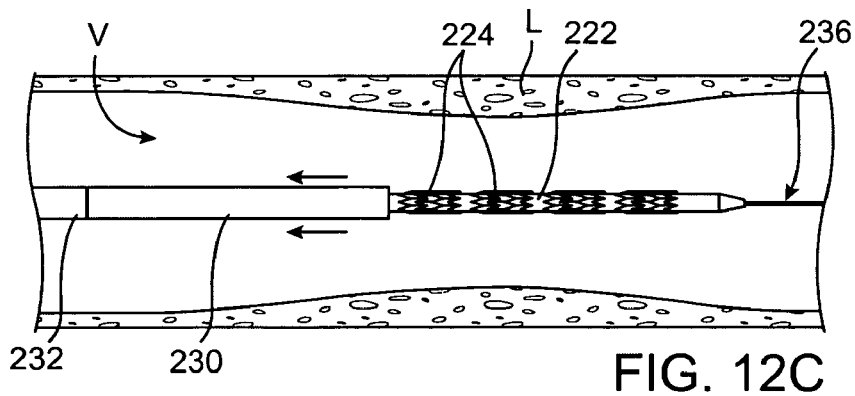
Figure 12D:
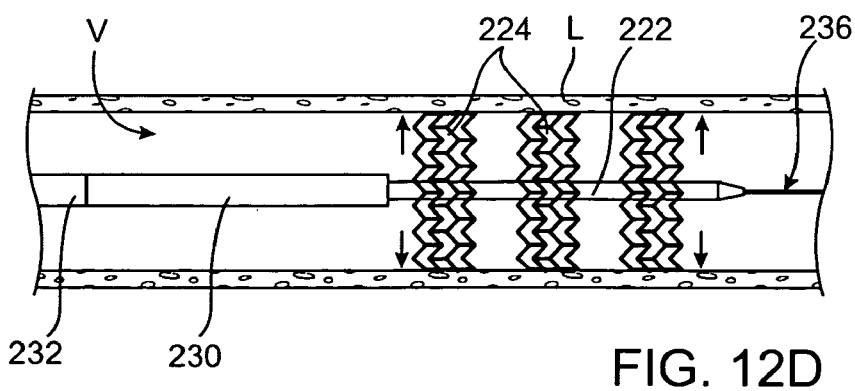
Figure 12E:
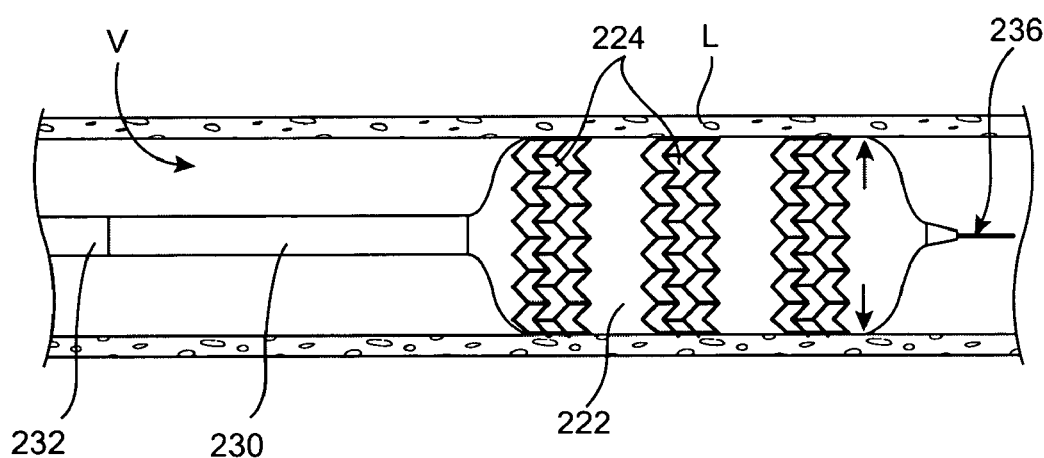

FIGS. 12A-12E show another embodiment of a method for dilating and placing a stent in a lesion L. A stent delivery catheter device 220 is advanced over a guidewire 236 to a position in a vessel V for treating the lesion L. In one embodiment, catheter device 220 includes an outer sheath 232 coupled with an outer expandable member 230, both of which are slidably disposed over an inner catheter body 221. As shown in FIG. 12B, outer expandable member 230 may then be expanded to contact and expand the portion of the vessel V containing the lesion. Outer expandable member 230 may then be deflated and retracted, along with outer sheath 232, as shown in FIG. 12C. Retracting outer sheath 232 and outer expandable member 230 may expose a stent having one or more stent segments 224 as well as an inner expandable member 222. In one embodiment, as shown in FIG. 12D, stent segments 224 may self-expand to contact the lesion. As shown in FIG. 12E an additional optional step may include expanding inner expandable member 222 to further dilate the lesion L, further expand segments 224, assure expansion of segments 224 and/or the like.

A number of additions, variations and modifications of the method just described may be made in various embodiments. For example, in an alternative embodiment, outer expandable member 230 may be moved distally after expansion of segments 224 and may be re-expanded to further expand segments. In such an embodiment, it may be necessary to have only one expandable member, such as outer expandable member 230. In other embodiments, such as described in relation to FIGS. 11A and 11B, only an inner expandable member is used. Also, in various embodiments any suitable combination and order of dilation and stent placement steps may be employed. Furthermore, various embodiments of the devices and methods described above for dilatation in combination with stent placement may be used with any of a variety of stents and stent delivery systems, including those described in U.S. patent application Ser. Nos. 10/306,622 and 10/306,620, both of which were filed on Nov. 27, 2002, and both of which are hereby fully incorporated by reference.

Therefore, although the above is complete description of the preferred embodiments of the invention, various alternatives, additions, modifications and improvements may be made without departing from the scope thereof. For example, while the foregoing description of the invention is directed to a stent delivery catheter for deploying stents into vascular lumens to maintain patency, various other types of wire-guided catheters also may embody the principles of the invention. For example, balloon catheters for angioplasty and other purposes, particularly those having a slidable external sheath surrounding the balloon, may be constructed in accordance with the invention. Other types of catheters for deployment of prosthetic devices such as embolic coils, stent grafts, aneurism repair devices, annuloplasty rings, heart valves, anastomosis devices, staples or clips, as well as ultrasound and angiography catheters, electrophysiological mapping and ablation catheters, and other devices may also utilize the principles of the invention. Thus, the above description is provided primarily for exemplary purposes and should not be interpreted to limit the scope of the claims as they are set forth below.

What is claimed is:

1. A stent delivery device for delivering at least one stent to a treatment site, the device comprising:
    a catheter shaft having a proximal end and a distal end;
    an expandable member coupled with the catheter shaft near the distal end;
    at least one stent slidably positionable on the expandable member; and
    at least one axially movable sheath disposed over at least part of the expandable member and stent thereon, wherein:
        the sheath is axially movable relative to the catheter shaft to expose at least a portion of the expandable member without exposing the stent;
        the exposed portion of the expandable member is expandable to dilate a lesion at the treatment site without expanding the stent;
        a length of the exposed portion of the expandable member is selected in situ; and
        the sheath is also movable to expose at least a portion of the stent to allow it to expand.

2. A device as in claim 1, wherein the stent is self-expanding.

3. A device as in claim 1, further including a pusher member for advancing the stent along the expandable member.

4. A device as in claim 1, wherein the stent comprises a plurality of separable, self-expanding stent segments.

5. A device as in claim 4, wherein the sheath is configured to constrain expansion of a first plurality of the stent segments while allowing expansion of a second plurality of the stent segments.

6. A device as in claim 5, wherein the sheath further comprises at least one separation device for separating the first plurality of stent segments from the second plurality, thus allowing for expansion of a stent segment without interfering with adjacent stent segments.

7. A device as in claim 4, wherein the stent segments comprise a thermal shape memory material, and wherein the expandable member is configured to accept one or more heated or cooled fluids to change a temperature of the stent segments.

8. A stent delivery device for treating a target site in a vessel, the device comprising:
    a catheter shaft having a proximal end and a distal end;
    a stent expansion member coupled with the catheter shaft near the distal end;
    a first stent slidably positionable on the expansion member and being deployable from the catheter shaft;
    a second stent slidably positionable on the expansion member and being deployable from the catheter shaft independently of the first stent; and
    a dilatation member for dilating the target site independently of deploying the first and second stents, the dilation member being independently expandable of the expansion member.

9. A stent delivery device for delivering at least one stem to a treatment site, the device comprising:
    a catheter shaft having a proximal end and a distal end;
    a stent expansion member coupled with the catheter shaft near the distal end;
    at least one stent positionable on the stent expansion member;
    at least one axially movable sheath disposed over at least part of the stem expansion member and stent thereon; and
    a dilatation member coupled with the sheath for dilating one or more lesions at the treatment site, the dilation member being expandable beyond a diameter of the sheath to dilate the one or more lesions at the treatment site and the dilation member being independently expandable of the expansion member.

10. A device as in claim 9, wherein the stent comprises a plurality of separable stent segments.

11. A device as in claim 10, wherein the separable stent segments are axially movable along the stent expansion member.

12. A device as in claim 11, further comprising a pusher member for advancing the stem segments axially along the stent expansion member.

13. A device as in claim 10, wherein the sheath is configured to constrain expansion of a first portion of the stent expansion member and a first plurality of the stem segments while allowing expansion of a second portion of the stem expansion member and a second plurality of the stent segments.

14. A device as in claim 13, wherein the sheath further comprises at least one separation device for separating the first plurality of stent segments from the second plurality, thus allowing for expansion of a stent segment by the stent expansion member without interfering with adjacent stent segments.

15. A device as in claim 9, further including at least one inflation lumen for expanding the dilatation member.

16. A device as in claim 15, wherein the inflation lumen comprises a tubular member disposed concentrically over the sheath.

17. A device as in claim 15, wherein the inflation lumen comprises a tubular member coupled with and extending along the outer surface of the sheath.

18. A device as in claim 15, wherein the inflation lumen is disposed within a wall of the sheath.

19. A method for delivering at least one stent to a treatment site, the method comprising:
    positioning a distal portion of a stent delivery catheter device at the treatment site, the stem delivery catheter comprising an expandable member and carrying at least one stent;
    retracting a sheath disposed over the expandable member to expose at least a portion of the expandable member;
    expanding the exposed portion of the expandable member to dilate at least a portion of a lesion at the treatment site;
    selecting a deployable portion of the stent having a selected length; and
    expanding the deployable portion of the stent at the treatment site, an undeployed portion of the stent remaining in the delivery catheter.

20. A method as in claim 19, further comprising positioning the deployable portion of the stem over the expandable member.

21. A method as in claim 19, wherein expanding the deployable portion of the stem comprises expanding the expandable member.

22. A method as in claim 19, wherein retracting the sheath also retracts the at least one stent relative to the expandable member.

23. A method as in claim 19, wherein the at least one stent comprises a plurality of stent segments, and wherein positioning at least the portion of the at least one stent over the expandable member comprises positioning at least one stent segment over the expandable member.

24. A method as in claim 23, wherein positioning the at least one stem segment over the expandable member comprises:
    allowing the expandable member to return to an unexpanded form; and
    retracting the unexpanded expandable member to a position within the at least one stent segment.

25. A method as in claim 24, further comprising retracting a sheath disposed over the expandable member and the plurality of stent segments to expose at least the portion of the expandable member and stent segments thereon.

26. A method for delivering at least one stent segment to a treatment site, the method comprising:
    positioning a distal portion of a stent delivery catheter device at the treatment site, the stem delivery catheter carrying at least one stent segment and comprising an expandable member and sheath;
    exposing a portion of the expandable member outside the sheath;
    expanding at least a portion of the expandable member on the catheter device to dilate at least a portion of a lesion at the treatment site; and
    retracting the sheath on the catheter device to expose at least a portion of the at least one stent from within the sheath, the portion self-expanding at the treatment site.

27. A method as in claim 26, wherein the at least one stent comprises a plurality of stent segments, and wherein retracting the sheath exposes at least one of the stem segments to self-expand at the treatment site.

28. A method as in claim 27, further comprising, after retracting the sheath:
    positioning the expandable member within the at least one self-expanded stent segment; and
    expanding at least a portion of the expandable member to further expand the stent segment.

29. A method as in claim 26, further comprising retracting the portion of the expandable member to a position within the sheath after the expanding step.

30. A method as in claim 26, further comprising passing a fluid through the expandable member while the at least one stent segment is disposed thereon, wherein the at least one stent segment comprises a thermal shape memory material, and wherein passing the fluid changes the temperature of the at least one stent segment.

31. A method as in claim 30, wherein the passed fluid is heated to a temperature higher than body temperature.

32. A method as in claim 30, wherein the passed fluid is cooled to a temperature lower than body temperature.

33. A method as in claim 30, wherein the portion of the expandable member is expanded using the fluid.

* * * * *

UNITED STATES PATENT AND TRADEMARK OFFICE
CERTIFICATE OF CORRECTION

PATENT NO. : 8,177,831 B2  
APPLICATION NO. : 12/027447  
DATED : May 15, 2012  
INVENTOR(S) : Bernard Andreas Page 1 of 1

It is certified that error appears in the above-identified patent and that said Letters Patent is hereby corrected as shown below:

In the Claims

Column 19, line 24, please delete "stem" and insert --stent--.

Column 19, line 32, please delete "stem" and insert --stent--.

Column 19, line 46, please delete "stem" and insert --stent--.

Column 19, line 50, please delete "stem" and insert --stent--.

Column 19, line 51, please delete "stem" and insert --stent--.

Column 20, line 6, please delete "stem" and insert --stent--.

Column 20, line 20, please delete "stem" and insert --stent--.

Column 20, line 23, please delete "stem" and insert --stent--.

Column 20, line 34, please delete "stem" and insert --stent--.

Column 20, line 47, please delete "stem" and insert --stent--.

Column 20, line 60, please delete "stem" and insert --stent--.

Signed and Sealed this  
Tenth Day of July, 2012

David J. Kappos  
*Director of the United States Patent and Trademark Office*